(12) United States Patent
Chang

(10) Patent No.: US 11,276,328 B2
(45) Date of Patent: Mar. 15, 2022

(54) AUTOMATIC INJECTION TRAINING DEVICE

(71) Applicant: CAREBAY EUROPE LTD, Sliema (MT)

(72) Inventor: Yun-Hsuan Chang, Bade (TW)

(73) Assignee: SHL MEDICAL AG, Zug (CH)

( * ) Notice: Subject to any disclaimer, the term of this patent is extended or adjusted under 35 U.S.C. 154(b) by 186 days.

(21) Appl. No.: 16/076,262

(22) PCT Filed: Jan. 24, 2017

(86) PCT No.: PCT/EP2017/051395
§ 371 (c)(1),
(2) Date: Aug. 7, 2018

(87) PCT Pub. No.: WO2017/144211
PCT Pub. Date: Aug. 31, 2017

(65) Prior Publication Data
US 2019/0266921 A1    Aug. 29, 2019

(30) Foreign Application Priority Data
Feb. 25, 2016 (SE) .................................... 1650249-4

(51) Int. Cl.
*G09B 23/28* (2006.01)
*A61M 5/32* (2006.01)
*A61M 5/20* (2006.01)

(52) U.S. Cl.
CPC ........... *G09B 23/285* (2013.01); *A61M 5/326* (2013.01); *A61M 2005/2013* (2013.01);
(Continued)

(58) Field of Classification Search
CPC .................................................... G09B 23/285
(Continued)

(56) References Cited

U.S. PATENT DOCUMENTS

| 5,071,353 A | 12/1991 | van der Wal |
| 5,567,160 A * | 10/1996 | Massino .............. G09B 23/285 434/262 |

(Continued)

FOREIGN PATENT DOCUMENTS

| CH | 709126 A2 | 7/2015 |
| TW | I498137 B | 9/2015 |

(Continued)

OTHER PUBLICATIONS

International Search Report and Written Opinion for Int. App. No. PCT/EP2017/051395, dated Apr. 3, 2017.

*Primary Examiner* — Thomas J Hong
(74) *Attorney, Agent, or Firm* — McDonnell Boehnen Hulbert & Berghoff LLP

(57) ABSTRACT

An automatic injection training device is presented having an elongated housing having a tubular demo container axially and rotationally fixed relative to the elongated housing and having a tubular wall, a reloadable plunger assembly having a plunger which is movable in the demo container between a first and a second position and a first energy accumulating member that moves the plunger from the first to the second position, an actuation assembly that holds the plunger in the first position, a biased needle cover that is movable in relation to the housing from an extended position to a retracted position and from the retracted position to the extended position, wherein the needle cover member interacts with the actuation assembly for releasing the plunger when the needle cover member is moved distally.

20 Claims, 18 Drawing Sheets

(52) U.S. Cl.
CPC . *A61M 2005/3267* (2013.01); *A61M 2205/43* (2013.01); *A61M 2205/581* (2013.01); *A61M 2209/02* (2013.01)

(58) Field of Classification Search
USPC .......................................................... 434/262
See application file for complete search history.

(56) References Cited

U.S. PATENT DOCUMENTS

| | | | |
|---|---|---|---|
| 2007/0111175 A1 | 5/2007 | Raven et al. | |
| 2009/0312705 A1* | 12/2009 | Grunhut | A61M 5/326 604/110 |
| 2012/0015336 A1* | 1/2012 | Mach | A61M 5/20 434/262 |
| 2013/0267897 A1* | 10/2013 | Kemp | A61M 5/2033 604/131 |
| 2014/0276568 A1* | 9/2014 | Worden | G09B 23/285 604/506 |

FOREIGN PATENT DOCUMENTS

| | | |
|---|---|---|
| TW | I507222 B | 11/2015 |
| TW | I519331 B | 2/2016 |
| WO | 2014/056868 A1 | 4/2014 |
| WO | 2015/110327 A1 | 7/2015 |

\* cited by examiner

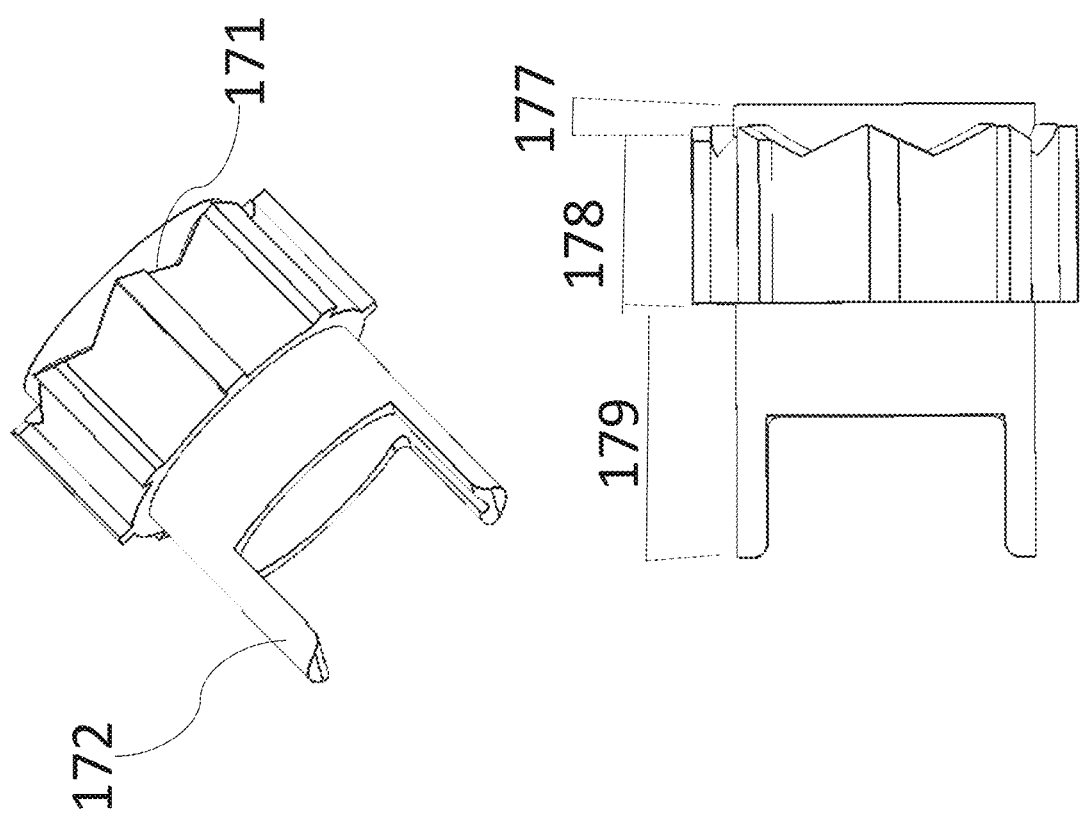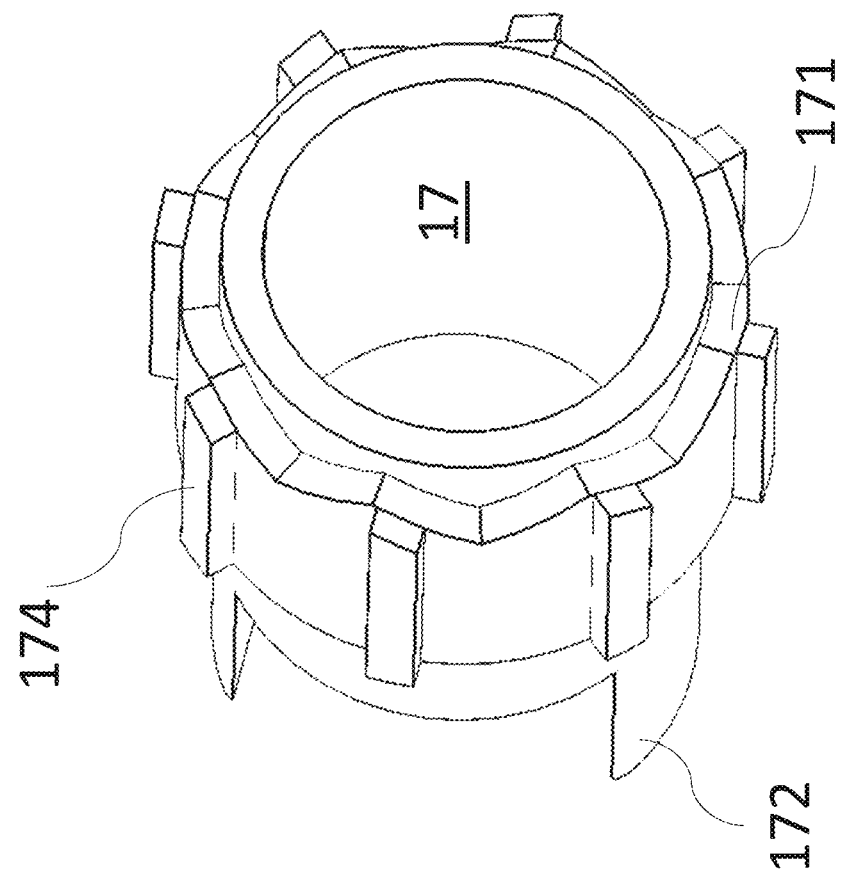
FIG.9

FIG.16
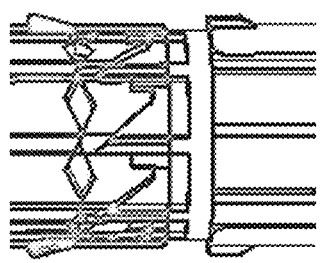
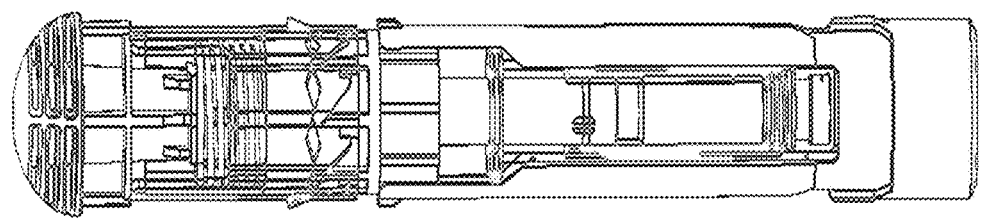
VI.
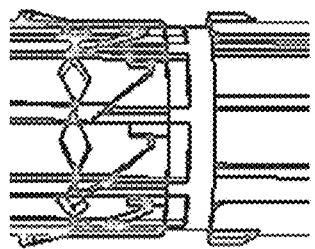
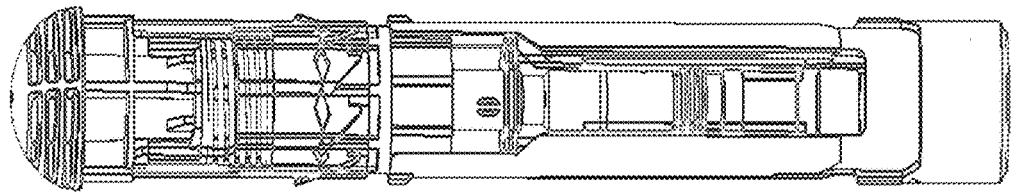
V.
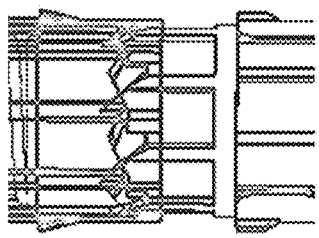
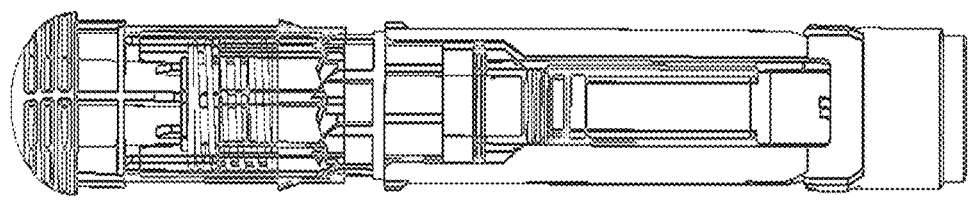
IV.

FIG.17
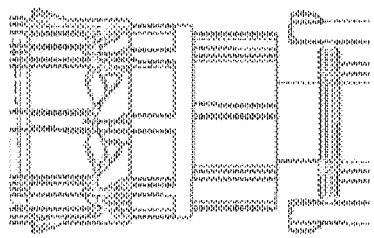
IX
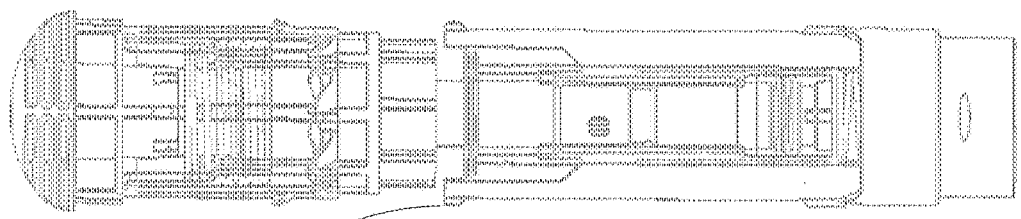
64
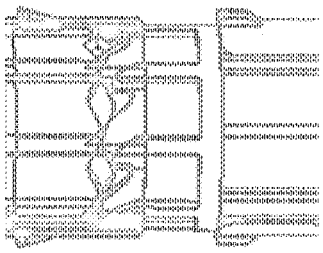
VIII
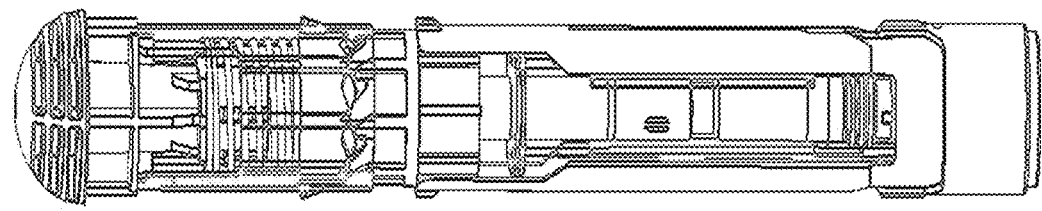
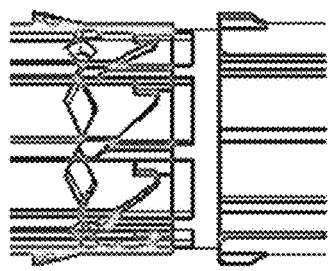
VII
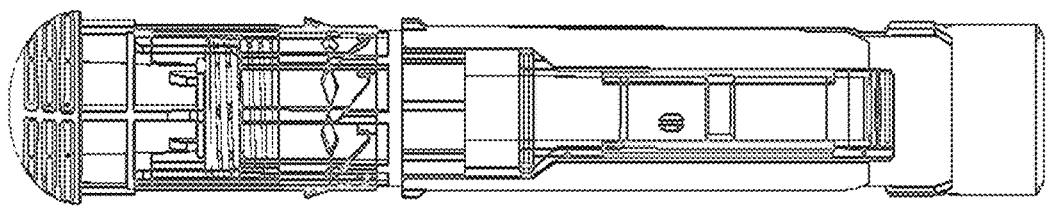

FIG.18
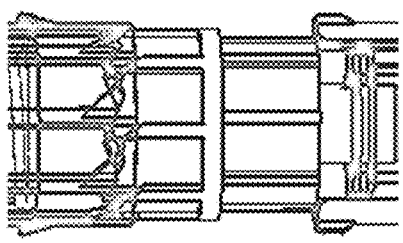
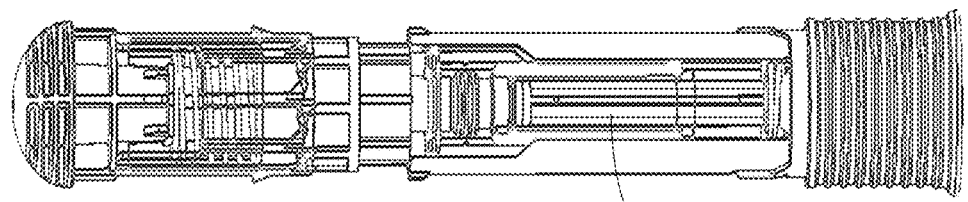
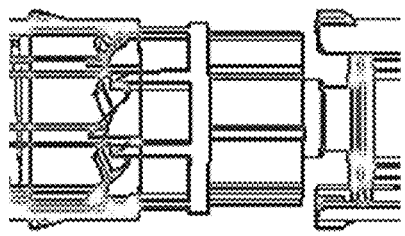
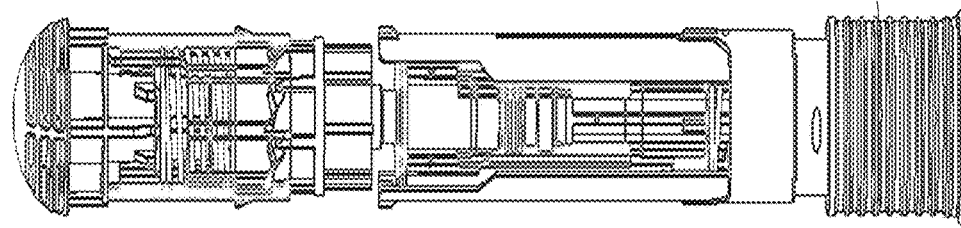
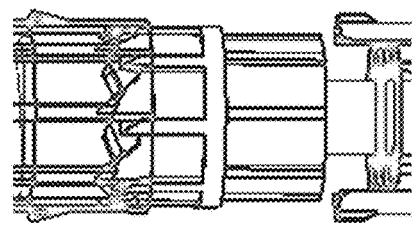
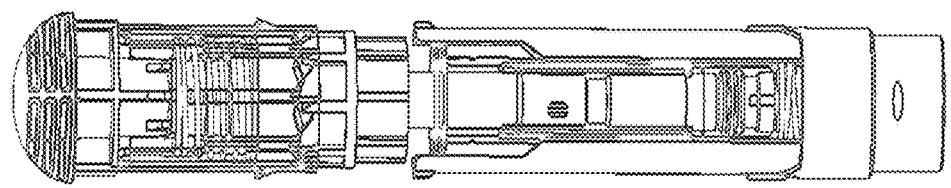

AUTOMATIC INJECTION TRAINING DEVICE

CROSS REFERENCE TO RELATED APPLICATIONS

The present application is a U.S. National Phase Application pursuant to 35 U.S.C. § 371 of International Application No. PCT/EP2017/051395 filed Jan. 24, 2017, which claims priority to Swedish Patent Application No. 1650249-4 filed Feb. 25, 2016. The entire disclosure contents of these applications are here with incorporated by reference into the present application.

TECHNICAL FIELD

The present disclosure relates to automatic injection training devices, i.e. educational appliances or dummies to train individuals in the administration of medication by means of automatic injection devices. More specifically, the present disclosure relates to a reloadable training device that simulates the different steps during a simulated injection process.

BACKGROUND

Automatic injection devices for delivering active substances are well known in the art. In many cases, training versions of such devices are required for showing potential users (e.g., patients or healthcare providers) how a device should be employed and for illustrating the advantages of the device. Such devices are frequently called "promotion" or "training" devices. The devices should mimic the function of different steps corresponding to a real injection device, but should not be capable of injecting an active substance.

Document U.S. Pat. No. 5,071,353 describes a training device for an automatic injector. The device comprises a cylindrical outer sleeve in the rear position of which a discharge mechanism is connected. The discharge mechanism comprises a plunger, a coil spring which acts on the plunger, a locking device, and a safety member. However, this device does not provide means allowing an accurate simulation of the resistance acting on the discharge mechanism of a regular injection device when an active substance is ejected or a simulation that the needle cover is locked after the simulated injection.

SUMMARY

The aim of the present disclosure is to obtain an improved automatic injection training device that simulates different steps during a simulated injection process.

This aim is solved according to the present disclosure by a medicament delivery device according to the features of the independent patent claim.

Preferable embodiments form the subject of the dependent patent claims.

According to the main aspect of the disclosure it is characterised by an automatic injection training device that is reliable and easy to use when handling and activating. This is achieved by an automatic injection training device comprising: an elongated housing having a distal and an opposite proximal end and extending along a longitudinally axis (L); a tubular demo container axially and rotationally fixed relative to the elongated housing and having a tubular wall extending along the longitudinally axis (L); a reloadable plunger assembly comprising a plunger which is movable in the demo container between a first and a second position and a first energy accumulating member configured to move the plunger from the first to the second position; an actuation assembly configured to hold the plunger in the first position and to release the plunger from the first position; a first signal generating member releasably connected to the plunger and a signal generating member fixedly connected to the plunger, and wherein each signal generating member is configured to interact independently from each other for generating audible feedback signals; a biased needle cover assembly which is rotationally locked but axially movable in relation to the housing between an extended position, a retracted position and returned to the extended position. The automatic injection training device of the disclosure enhances the injection effect by coordinating the assemblies in a single ejection and retraction performance. The needle cover assembly of the training device is configured to interact with the actuation assembly for releasing the plunger when it is moved from the extended position to the retracted position and for preventing the needle cover assembly to be moved when it is returned to the extended position attaining a uniform and constant acceleration of the plunger when actuating on the proximal portion end of the needle cover member, which in turn hits in a single movement the injection site.

According to another aspect of the disclosure the actuation assembly of the training device comprises an actuator member and an actuator base which are fixedly connected to the elongated housing. The actuator sleeve is configured to interact with the actuator base and a second energy accumulating member, which is arranged between the actuator sleeve and the actuator member, and a rotator sleeve configured to interact with both the actuator member and the actuator base, and with the actuator sleeve. This arrangement of the actuator assembly allows a significant improvement in relation to the regulation of the rotational movement between the members.

In one aspect of the disclosure, the automatic injection training device biased needle cover assembly further comprises a third energy accumulating member in the form of a compression spring, for urging the needle cover member towards the proximal end of the elongated housing such that a proximal portion end of the needle cover protrudes from the proximal end of the elongated housing, and wherein the needle cover member has a distal edge and a locking protrusion operationally associated with the rotator sleeve. The contraction and retraction load of the accumulating member increases the sum of the resulting forces towards the injection site. One additional task of the arrangement is essentially to start the reload of the training device when pressed by the reload cap unit.

In an further embodiment of the disclosure disclosure, the automatic injection training device actuator sleeve is rotationally locked but axially movable in relation to the actuator base and operationally associated with the second energy accumulating member in the form of a compression spring such that, the actuator sleeve is axially moveable in relation to the actuator base against an axial force from said second energy accumulating member. An opposite force is achieved due to the accumulating member, which promotes the mechanical activation of the actuator parts abutted to the rotator sleeve.

In another embodiment, the injection training device actuator member comprises a resilient portion with a first segment, a second segment, and a tapering segment between the first segment and the second segment, and an annular inwardly directed ledge. This specific construction of the actuator attains the desired accelerated effect on the plunger whereas producing an audible signal in a reliable way.

An automatic injection training device of the disclosure disclosure may be provided with a rotator sleeve comprising a distal part, a central part and a proximal part on its outer surface and a first and a second circumferential chambers on its inner surface, wherein the distal part is rotatable and slidable connected to both the actuator base and to the actuator member and wherein the first and the second circumferential chambers are configured to interact with the second segment of the actuator member. To allocate the expansion and compression of the second segment of the actuator member to a single part (rotator sleeve) assures a proper operationally load/reload performance.

The proximal part of the rotator sleeve of another embodiment of the disclosure comprises longitudinally and equidistant extending ribs configured to interact with the locking protrusion of the needle cover member, wherein the central part of the rotator sleeve comprises a circumferential ledge configured to interact with the distal edge of the needle cover member ensuring a periodical connection between the two parts. The distal part of the rotator sleeve comprises also a distal facing circumferential crown gear surface configured to interact with a corresponding proximal facing circumferential crown gear surface of the actuator sleeve and longitudinally and equidistant extending ribs configured to interact with a guiding track on the inner surface of the actuator base. A controlled rotation of the rotator sleeve is achieved by the synergistic effect of the crown gear surfaces resulting in an improved effect on the needle cover locking protrusions.

The automatic injection training device actuator base further comprises a guiding track having a continuous sawtooth wave pattern track formed by a slanted edge where at its highest point passes to a longitudinally and proximally extending edge and where at the lowest point of the longitudinally extending edge passes to a minor slanted edge and where at the highest point of the minor slanted edge passes to a minor longitudinally and proximally extending edge. The guiding track configuration of the actuator base is aimed to lead safely the ribs of the rotator sleeve when rotating, resulting in a periodical path.

In another embodiment of the disclosure, the injection training device actuator member second segment is configured to interact with the first circumferential chamber of the rotator sleeve such that the annular inwardly directed ledge is engaged with an annular slot of the plunger for holding the plunger in the first position and wherein the second segment of the actuator member is configured to interact with the second circumferential chamber when the rotator sleeve is moved towards the distal end by pressing the needle cover member against an intended injection site, such that the second segment is flexed radially outwards impacting the second circumferential chamber for causing a first audible feedback signal which simulates the start of an injection phase. To produce an audible signal is significant for the user training program and as a sign to begin the injection operation.

The automatic injection training device further comprises a signal generating member which is fixedly connected to the proximal end of the plunger and configured to impact a proximal surface of the demo container or a proximal surface of the elongated housing when the proximal end of the plunger reaches the second position causing a second audible feedback signal which simulates the end of an injection phase. This second audible signal works as an announcement for the user that the injection has been performed successfully.

In a further embodiment of the disclosure, the automatic injection training device plunger comprises a friction element configured to interact with the tubular wall of the demo container such that when the plunger is released from the first position, a frictional resistive force between the friction element and the tubular wall of the demo container causes the plunger to be moved with a uniform speed and resistance simulating an injection phase of a medicament delivery. This frictional resistive force acts on the plunger increasing its velocity and improving the strike against the injection site.

The automatic injection training device demo container further comprises a tubular wall and a friction element configured to be released from each other a predetermined distance before the plunger reaches the second position causing the movement of the plunger to be accelerated. This accelerating effect is due to the different diameters, which in turn results in a propulsive force pushing forwards the plunger.

The plunger of the injection training device may further be axially moveable in relation to the elongated housing towards the distal end of the elongated housing from the second position to the first position against the axial force from the first energy accumulating member. The plunger freedom to retract to the original position (first position) is essential for the recharge of the injection device, an important feature for the repetitive use of the device during injection training.

In another embodiment of the disclosure, an assembly comprising an automatic injection training device having the features previously described above is provided with a reload cap unit. The reload cap unit comprises a removable proximal cap and a shaft member. Said reload cap unit is configured for being introduced into the elongated housing assembly through a proximal opening of the needle cover. The user can easily and safely recharge the injection device manually, due to the compression effect on the plunger, pushing backwards the first energy accumulation member until the second segment of the actuator member returns to the initial placement on the first chamber.

The assembly removable proximal cap comprises a first portion with a cup-shaped structure that is configured to accommodate and/or guide the proximal portion end of the needle cover that extends from the proximal end of the elongated housing and that is configured to bear against an abutment surface of the elongated housing assembly when the device is reloaded. Such interaction facilitates the expansion of the third accumulation member within the needle cover member.

These and other aspects of and advantages with the present disclosure will become apparent from the following detailed description and from the accompanying drawings.

BRIEF DESCRIPTION OF THE DRAWINGS

In the following detailed description of the disclosure, reference will be made to the accompanying drawings, of which:

FIG. 9 illustrates two perspective views and one side view of the actuator sleeve.

FIG. 18 (XI-XII) shows the mechanical sequence of the device of FIG. 1 with the distal cap and the shaft member when reloading.

DETAILED DESCRIPTION

In the present application, when the term "distal part/end" is used, this refers to the part/end of an automatic injection training device, or the parts/ends of the members thereof, which is/are located the furthest away from the medicament delivery site of the patient. Correspondingly, when the term "proximal part/end" is used, this refers to the part/end of the automatic injection training device, or the parts/ends of the members thereof, which, is/are located closest to the medicament delivery site of the patient.

Figure 1:
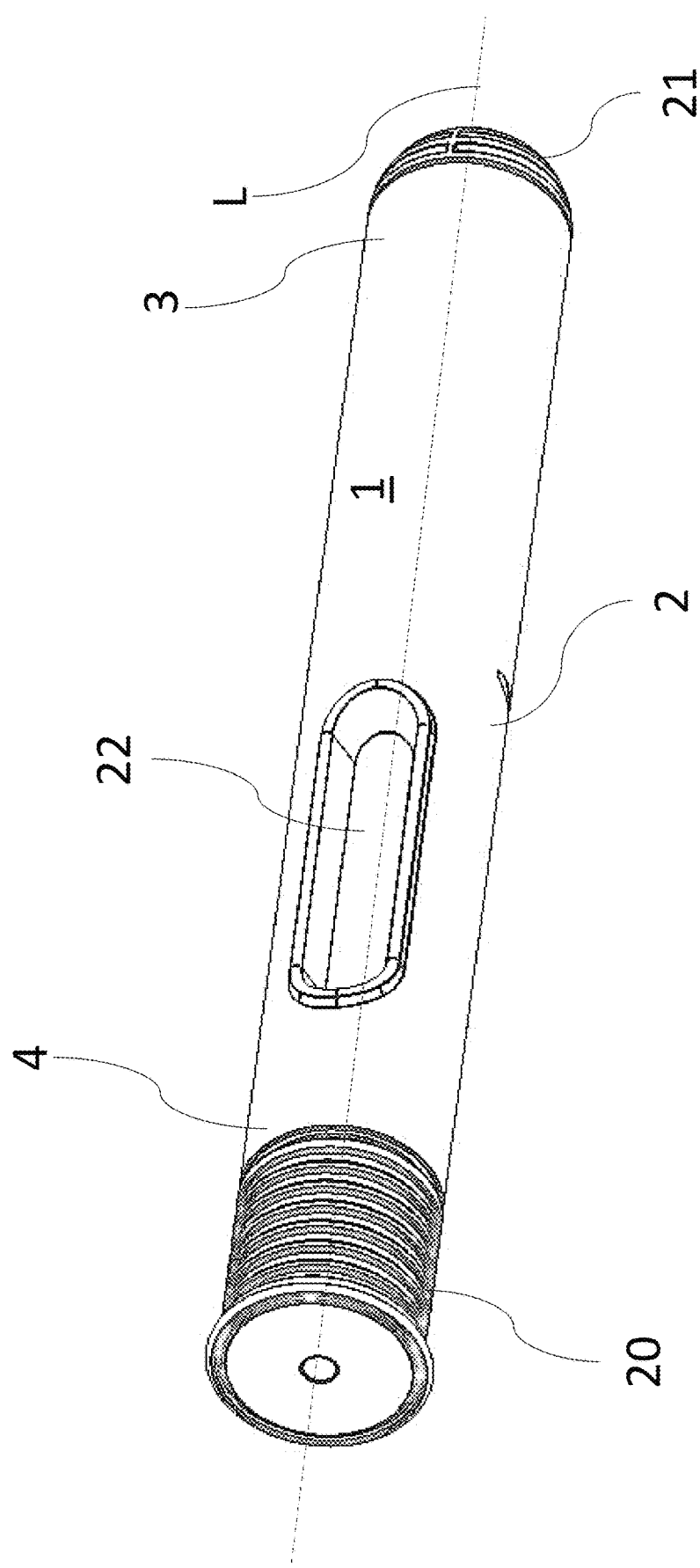
FIG. 1 shows a perspective view of one embodiment according to the present disclosure disclosing an automatic injection training device.

In FIG. 1 is shown an automatic injection training device 1 according to one embodiment of the present disclosure. The automatic injection training device 1 comprises an elongated housing 2, a reload cap 20 and a distal cap 21 extending along a longitudinal axis L, the caps (20, 21) seal the training device. The elongated housing 2 may also comprise an inspection window 22 for assessing visually the current state of the injection training device. Additionally, the elongated housing 2 has a distal end 3 and a proximal end 4.

Figure 2:
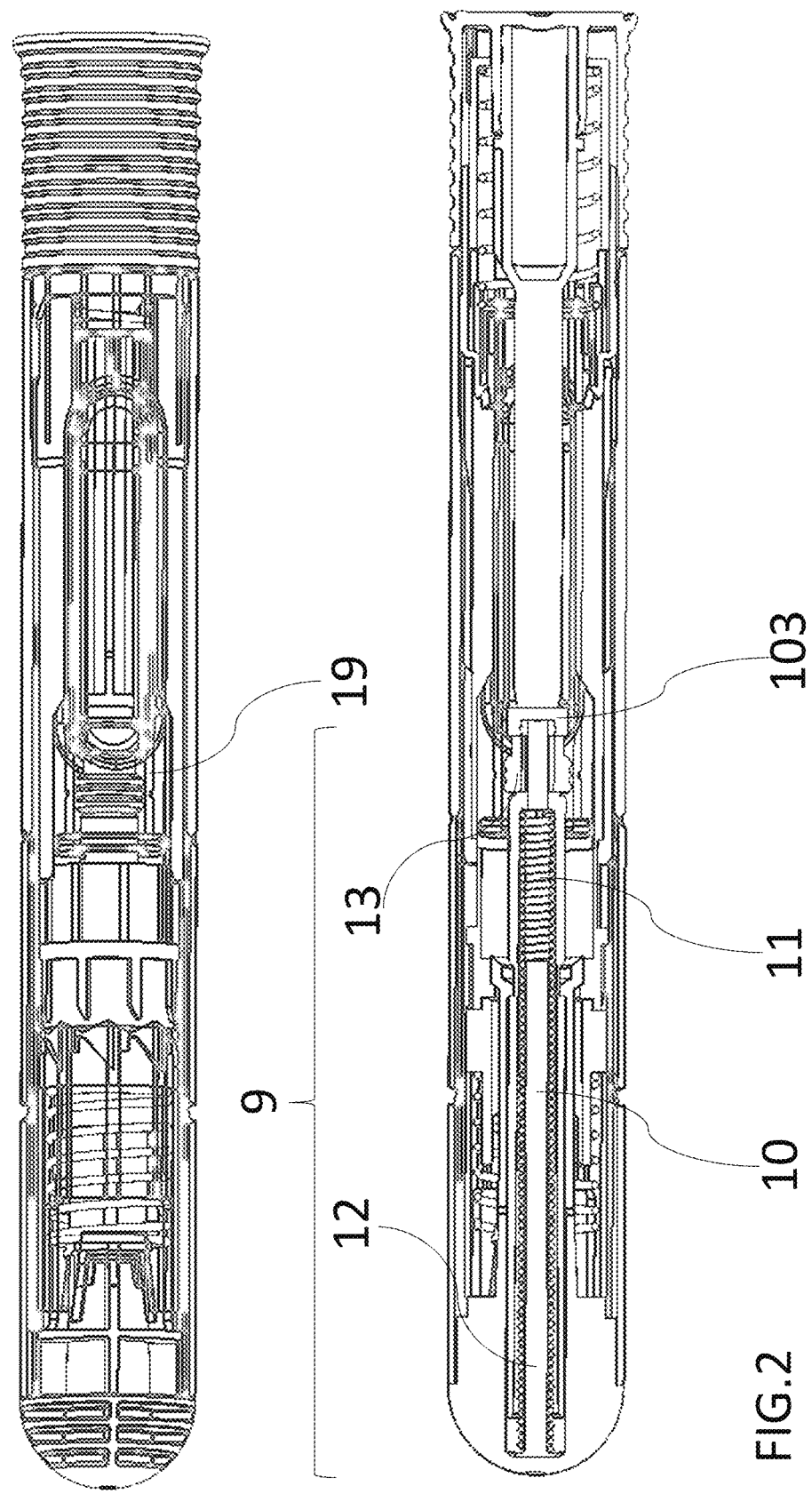
FIG. 2 shows a cross sectional view and a side view of the training device of FIG. 1 with the reload cap unit.

In FIG. 2, the device of the disclosure further comprises a tubular demo container 19 which is fixed to the elongated housing 2 by connecting means or members known in the art. More particularly the elongated housing 2 axially and rotationally fixed relatively to the elongated housing 2 and it extends along the longitudinally axis (L).

Furthermore, FIG. 2 illustrates the device of the disclosure comprising among others, a reloadable plunger assembly 9, comprising a plunger 10 with a friction element 13, the plunger 10 is movable in the demo container 19 between a first and a second position, a first energy accumulating member 11 is positioned co-axially within the plunger 10 and configured to move the plunger 10 from the first to the second position, and a piston rod 12 is positioned co-axially within the first energy accumulating member 11. In the present embodiment, the first energy accumulating member 11 is a compression spring. In FIG. 2 is also shown a signal generating member 103 which is fixedly connected to the proximal end of the plunger 10.

Figure 3:
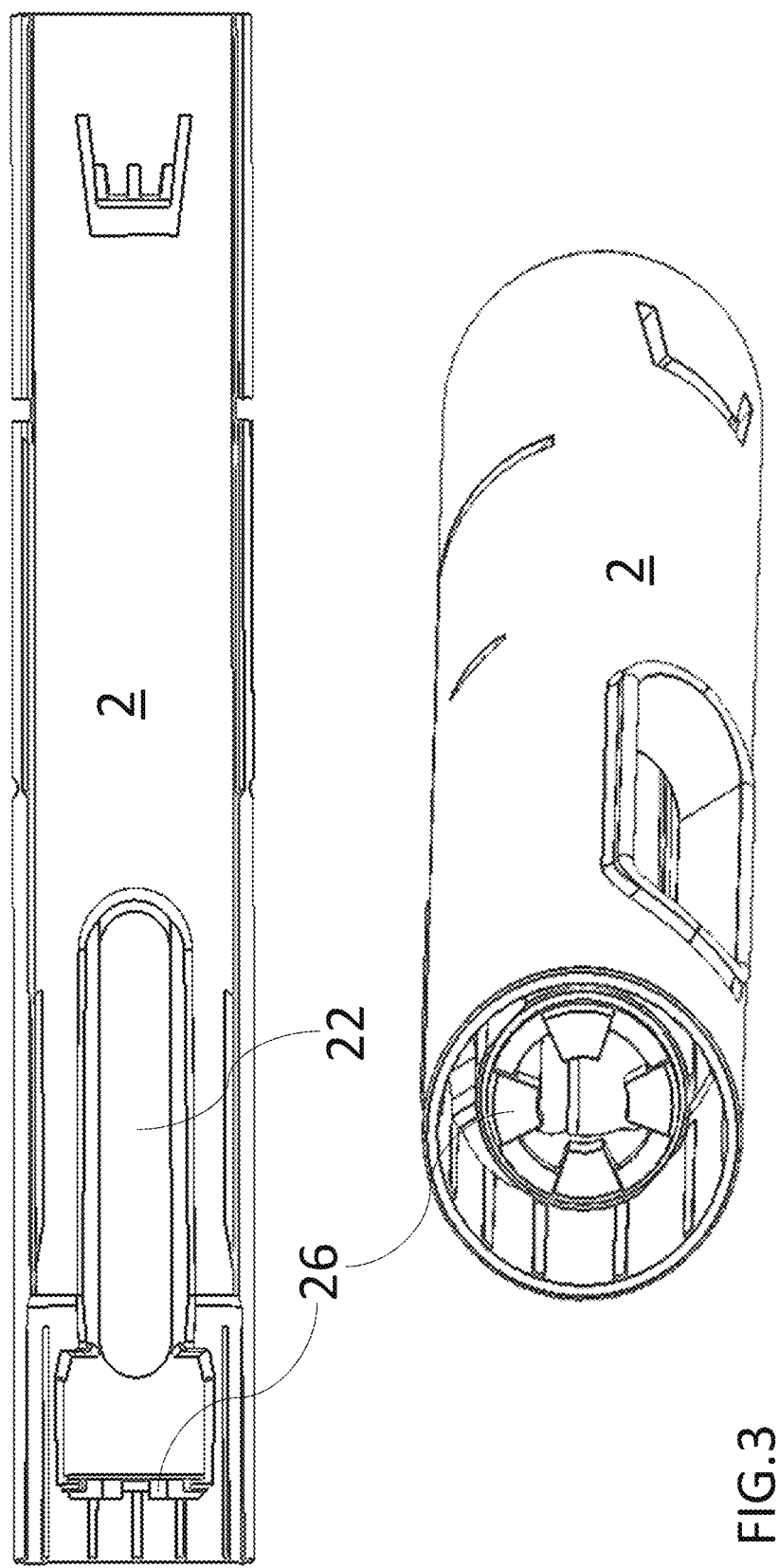
FIG. 3 shows a cross sectional view and a perspective view of the elongated housing.

A cross sectional view of the elongated housing 2 is depicted in FIG. 3. It illustrates inwardly the inspection window 22, and proximal stop flaps 26 of the elongated housing 2. The stop flaps 26 abut proximal end of the tubular demo container 19 or contacts with the plunger 10 signal generating member 103. FIG. 3 shows also a frontal side view of the elongated housing 2, wherein the proximal stop flaps 26 can be observed.

Figure 4:
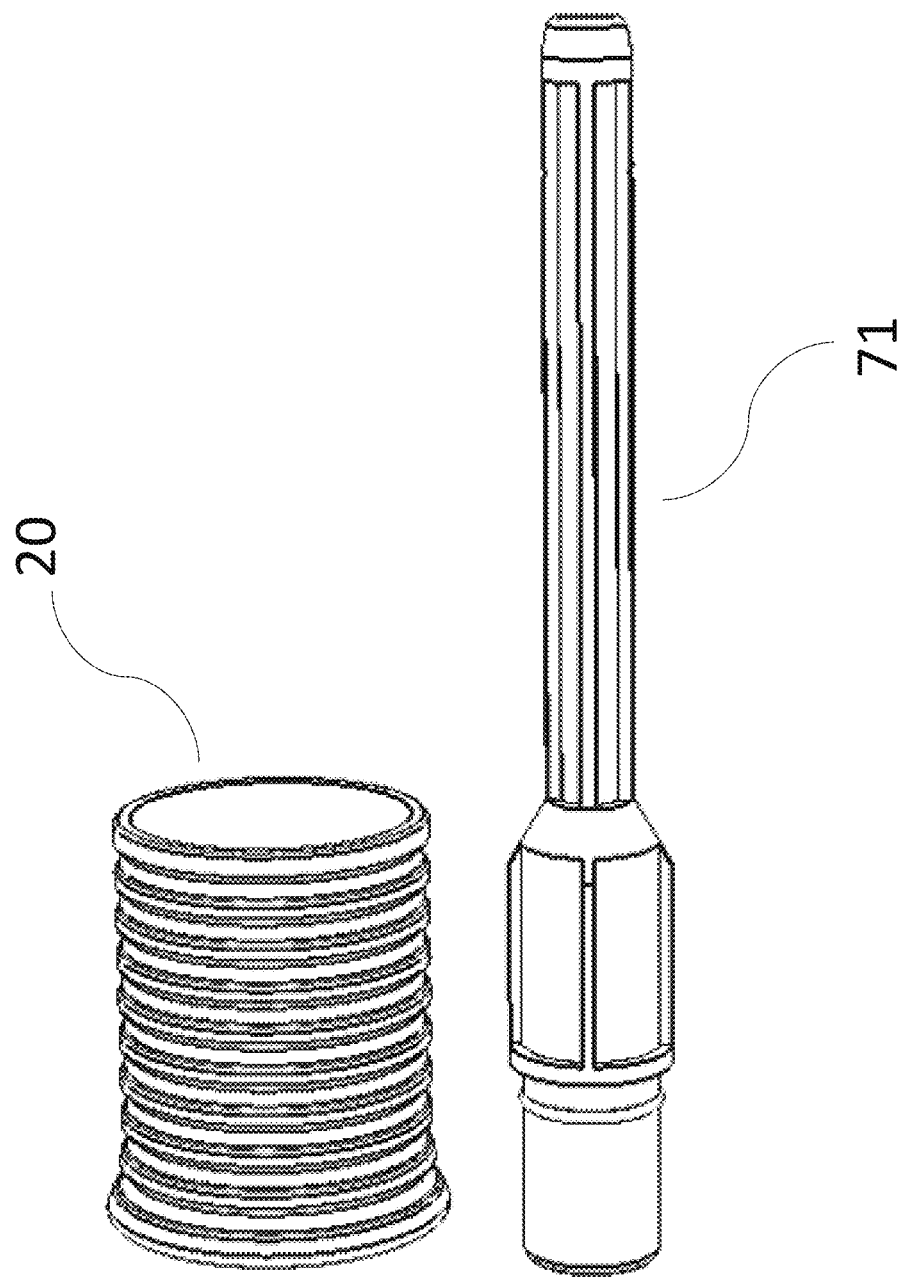
FIG. 4 shows a perspective view of the reload cap unit, namely the proximal cap and the shaft member of the previous embodiment.

The reload cap unit 5 is illustrated in FIG. 4 comprising the reload cap 20 and a shaft member 71. Before the injection training is placed on the injection site, the reload cap unit 5 is completely removed. The reload cap 20 may be adapted to be removably connected to the proximal end of the housing 2. Additionally, the shaft member 71 is aimed to push backwards the plunger 10 during reloading operation. The cap 20 and the shaft 71 can be attached or detached for easy handling by the user during reload operation or to facilitate the assembly operation during manufacture of the device of the disclosure. The shaft member 71 is configured for being introduced into the elongated housing 2 through a proximal opening of the needle cover 6 when reloading action is required.

Figure 5:
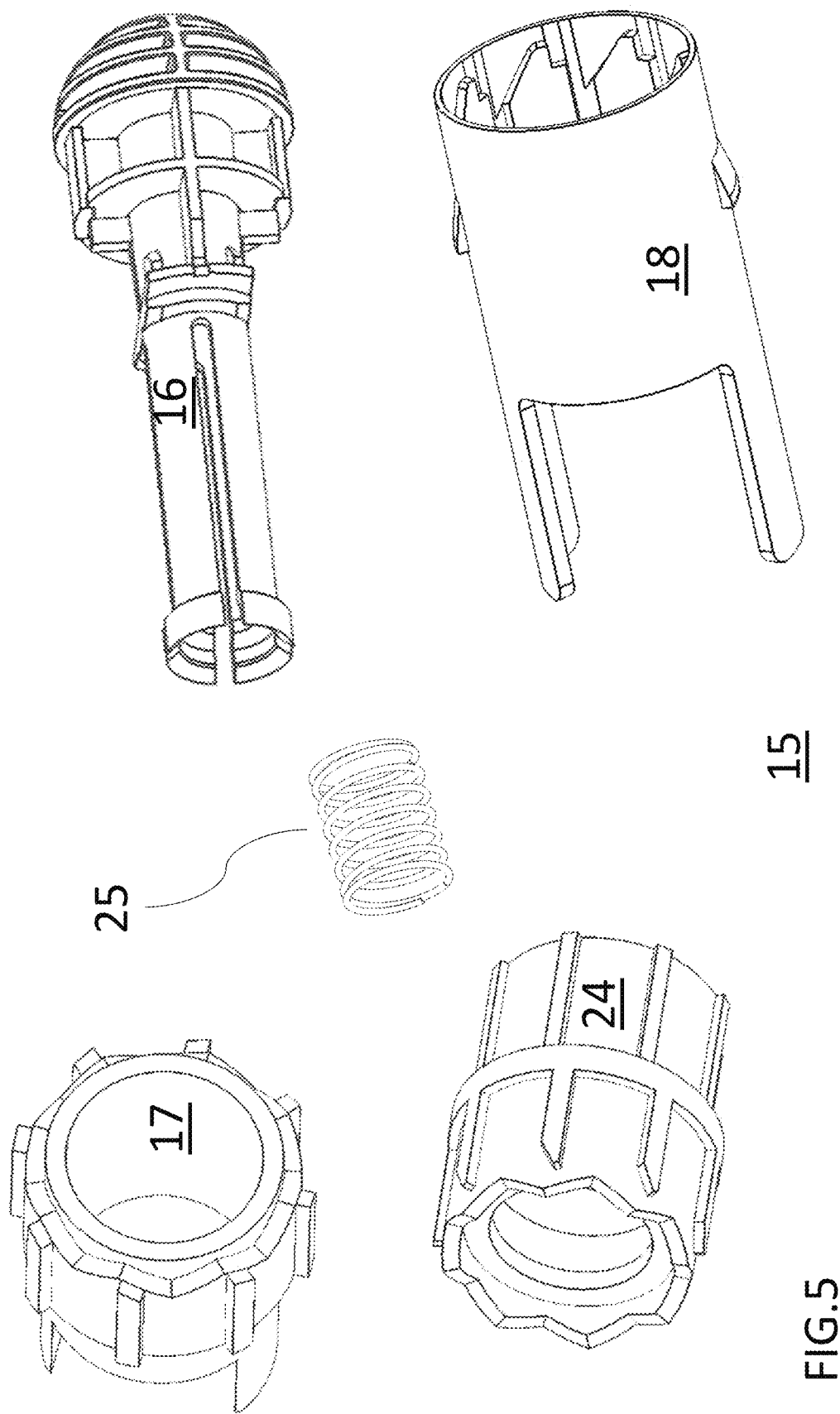
FIG. 5 discloses in perspective views the parts of the actuation assembly, viz. actuator sleeve, actuator member, actuator base, rotator sleeve and $2^{nd}$ accumulating member.

The device also comprises an actuation assembly 15 as shown in FIG. 5, configured to hold the plunger 10 in the first position and to release the plunger 10 from the first position. The actuation assembly 15 comprises an actuator member 16 and an actuator base 18 which are fixedly connected to the elongated housing 2 by suitable connecting means/members. Further the actuation assembly comprises an actuator sleeve 17 configured to interact with the actuator base 18. A second energy accumulating member 25 is arranged between the actuator sleeve 17 and the actuator member 16, and a rotator sleeve 24 is configured to interact with both the actuator member 16 and the actuator base 18, and with the actuator sleeve 17.

Figure 6:
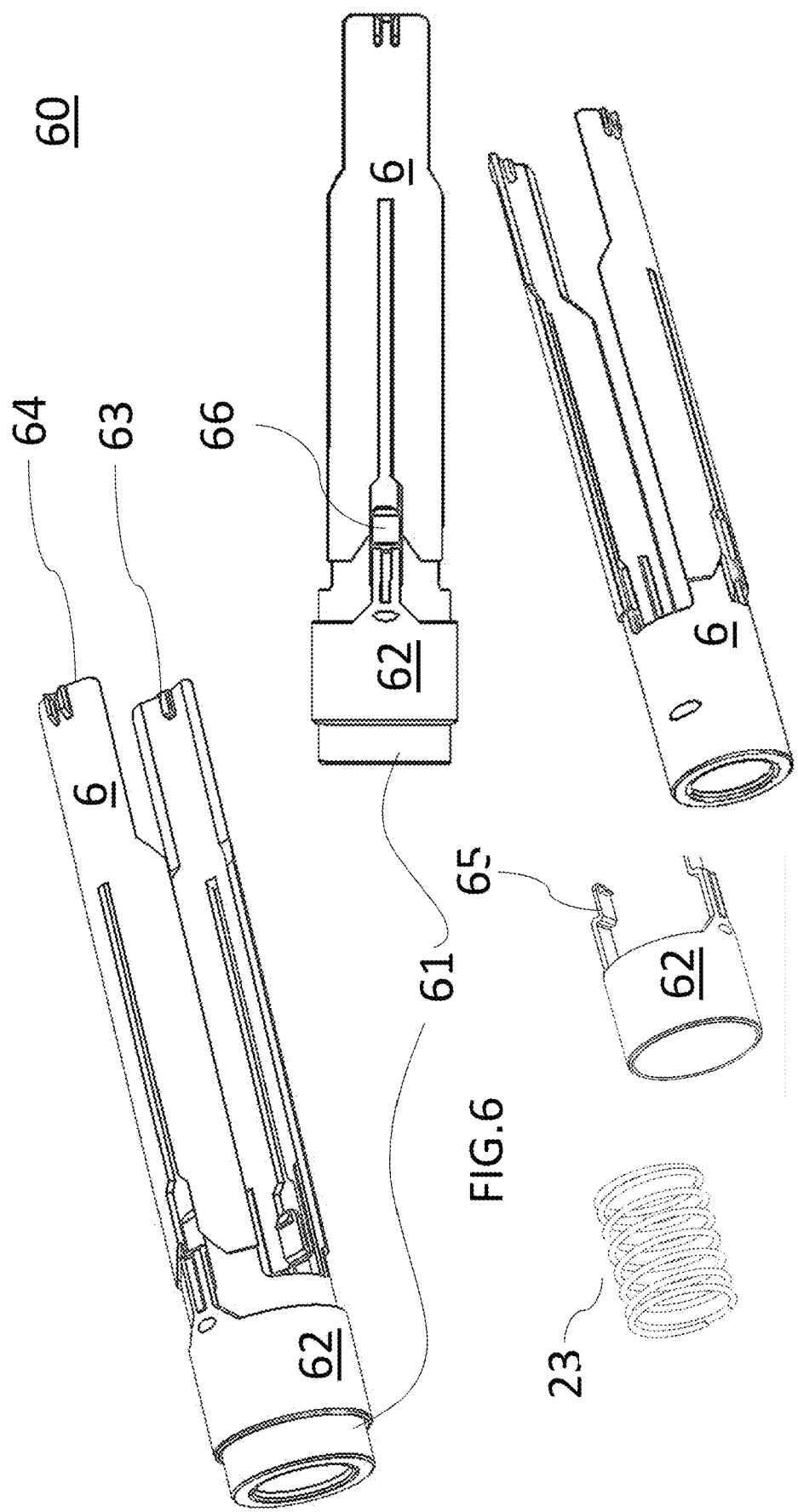
FIG. 6 illustrates the needle cover member, proximal portion and $3^{rd}$ accumulation member. Perspective and side view of the needle cover assembly are depicted with the parts attached and detached.

FIG. 6 discloses a needle cover member 6 and a third energy accumulation member cooperating operationally to enhance the injection training device effect. The needle cover member 6 can be equipped with a detachable proximal portion 62. The proximal portion 62 is abutted between the external proximal part of the needle cover member 6 and the internal proximal part of the elongated housing 2 securing the axial movement of the needle cover member 6 along the longitudinally axis (L) towards the injection site. Additional figures in FIG. 6 illustrates the needle cover member 6 attached with the proximal portion 62 by two extending tongues 65 connected to corresponding grooves 66 of the needle cover member 6.

The device biased needle cover assembly 60 comprises the needle cover member 6 which is rotationally locked but axially movable in relation to the housing 2 from an extended position to a retracted position and from the retracted position to the extended position, wherein the needle cover member 6 is configured to interact with the actuation assembly 15 for releasing the plunger 10 when the needle cover member 6 is moved from the extended position to the retracted position and for preventing the needle cover member 6 to be moved further when it is moved from the retracted position to the extended position. The third energy accumulating member 23 urges the needle cover member 6 towards the proximal end such that most of the proximal portion 62 of the needle cover 6 protrudes from the proximal end 4 of the elongated housing 2. The third energy accumulating member 23 is arranged between an inner proximal ledge of the needle cover member 6 and an inner ledge of the housing 2. The extended position of the needle cover member 6 is characterized by the position of the needle cover member 6 in relation to the housing 2 where most of the proximal portion 62 of the needle cover member 6 protrudes from the proximal end 4 of the housing 2. The retracted position of the needle cover member 6 is characterized by the position of the needle cover member 6 in relation to the housing 2 where a minor part of the proximal portion 62 of the needle cover member 6 protrudes from the proximal end 4 of the housing 2 or where the proximal end and transversal surface of the needle cover member 6 is flush with the proximal end and transversal surface of the housing 2. The needle cover member 6 has a distal edge 64 and a locking protrusion 63 operationally associated with the rotator sleeve 24.

Figure 7:
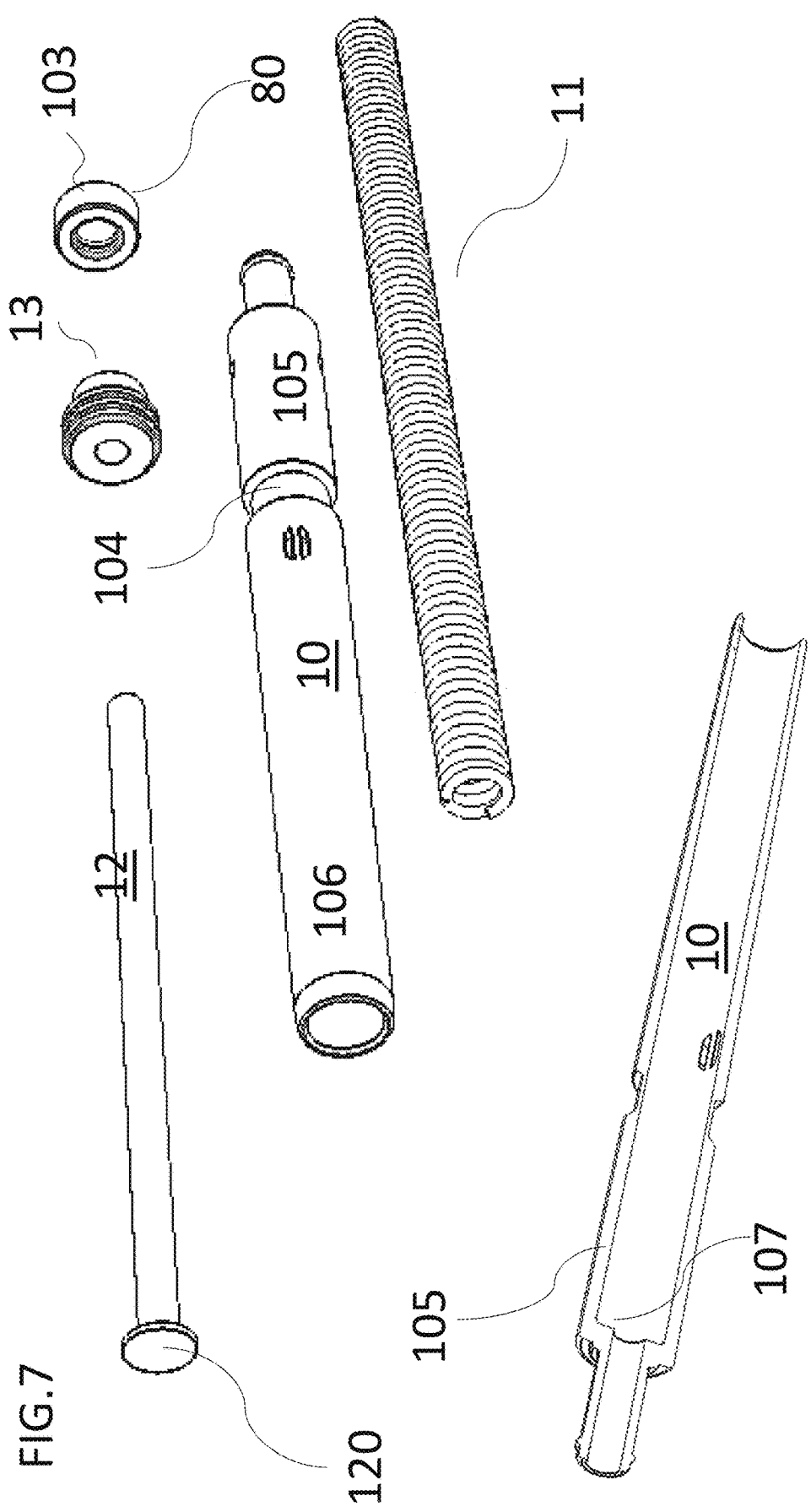
FIG. 7 shows an exploded perspective view of the reloadable plunger assembly and a cross-sectional view of the plunger.

The plunger 10 assembly is depicted in a first exploded figure and in a second cross sectional figure in FIG. 7. The plunger 10 is a hollow plunger and comprises a circumferential outer surface. The plunger 10 further comprises on its outer surface, a first proximal annular portion 105, a second annular portion 106 and an annular groove 104 between the first and the second portions. The plunger also comprises on in its inner surface an annular heel 107 to support the proximal end of the first energy accumulating member 11 as shown in the cross sectional figure. The signal generating member 103 comprises a proximal surface 80, which abuts against the proximal stop flaps 26 of the elongated housing 2 or the proximal end of the demo container 19. The plunger 10 further comprises a friction element 13 which may be a stopper arranged between the distal end of the signal generating member 103 and the proximal end of the annular portion 105. In FIG. 7 is also depicted a piston rod 12 having a distal annular flange 120. The distal end of the first energy accumulating member 11 is supported on the flange 120 of the piston rod 12 and this flange 120 is supported at a distal end and inner surface of the distal cap 21.

Figure 8:
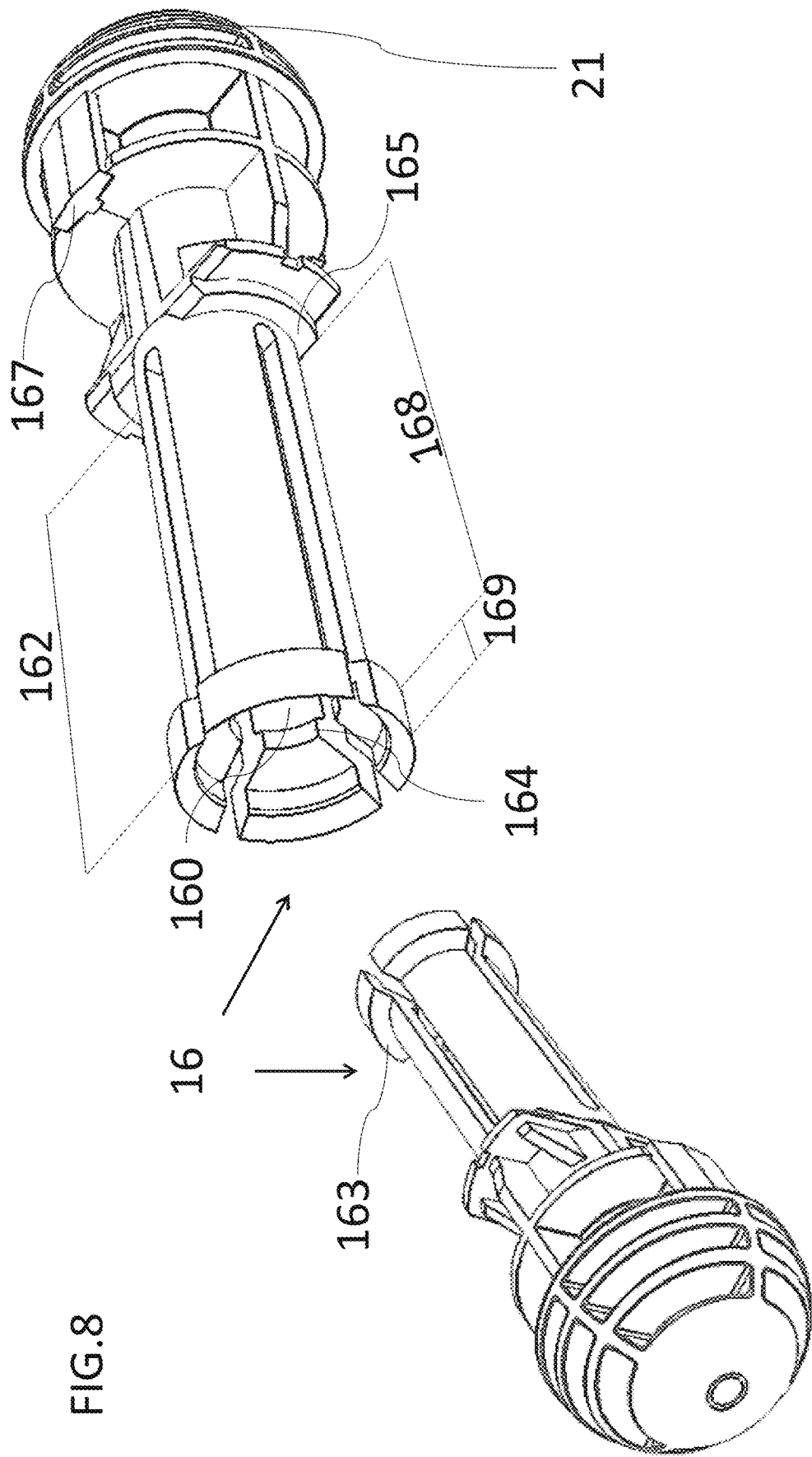
FIG. 8 illustrates two perspective views of the actuator member.

The actuator member 16 is illustrated in two different perspective views in FIG. 8. According to the embodiment of FIG. 1, the actuator member 16 is integrated to the distal cap 21 in one single part. However, it is also considered that the distal end of the actuator member 16 is axially and rotationally fixed to the distal cap 21 by suitable connecting members/means. The actuator member further comprises a resilient portion 162 which extends longitudinally towards the proximal end from the distal cap. The resilient portion 162 comprises a first segment 168, a second segment 169 and a tapering segment 163 between the first segment 168 and the second segment 169, and an annular inwardly directed ledge 164. In the present embodiment, the distal cap 21 comprises a fixed rotational ledge 167 configured to secure/fix the actuator member 16 to the housing. The actuator member 16 as illustrated in FIG. 8 further comprises a support element 165 and a central opening 160 extending along the longitudinal axis L and configured to receive the plunger 10. The resilient portion 162 with the first segment 168 has a first outer diameter and the second segment 169 has a second outer diameter, the second outer diameter being larger than the first outer diameter.

A perspective view of the actuator sleeve 17 is shown in FIG. 9. The actuator sleeve 17 comprises a distal section 179 having distal tongues 172, a proximal section 177, and a middle section 178. The middle section 178 has an outer diameter that is larger than the outer diameter of the proximal section 177 and the distal section 179. The outer circumference of the middle section 178 comprises equidistant longitudinal ribs 174. The proximal circumferential ledge between the proximal section 177 and the middle section 178 comprises a proximal facing circumferential crown gear surface 171 adapted to interact with a corresponding distal facing circumferential crown gear surface 247, FIG. 11, of the rotator sleeve 24 and the distal circumferential ledge between the distal section 179 and the middle section 178 is adapted to support the proximal end of the second energy accumulating member 25. The distal end of the second energy accumulating member 25 is supported by the support element 165 of the actuator member 16. The proximal facing circumferential crown gear surface 171 and the distal facing circumferential crown gear surface 247 comprise peaks, troughs and slanted edges arranged for functionally cooperation movement.

Figure 10:
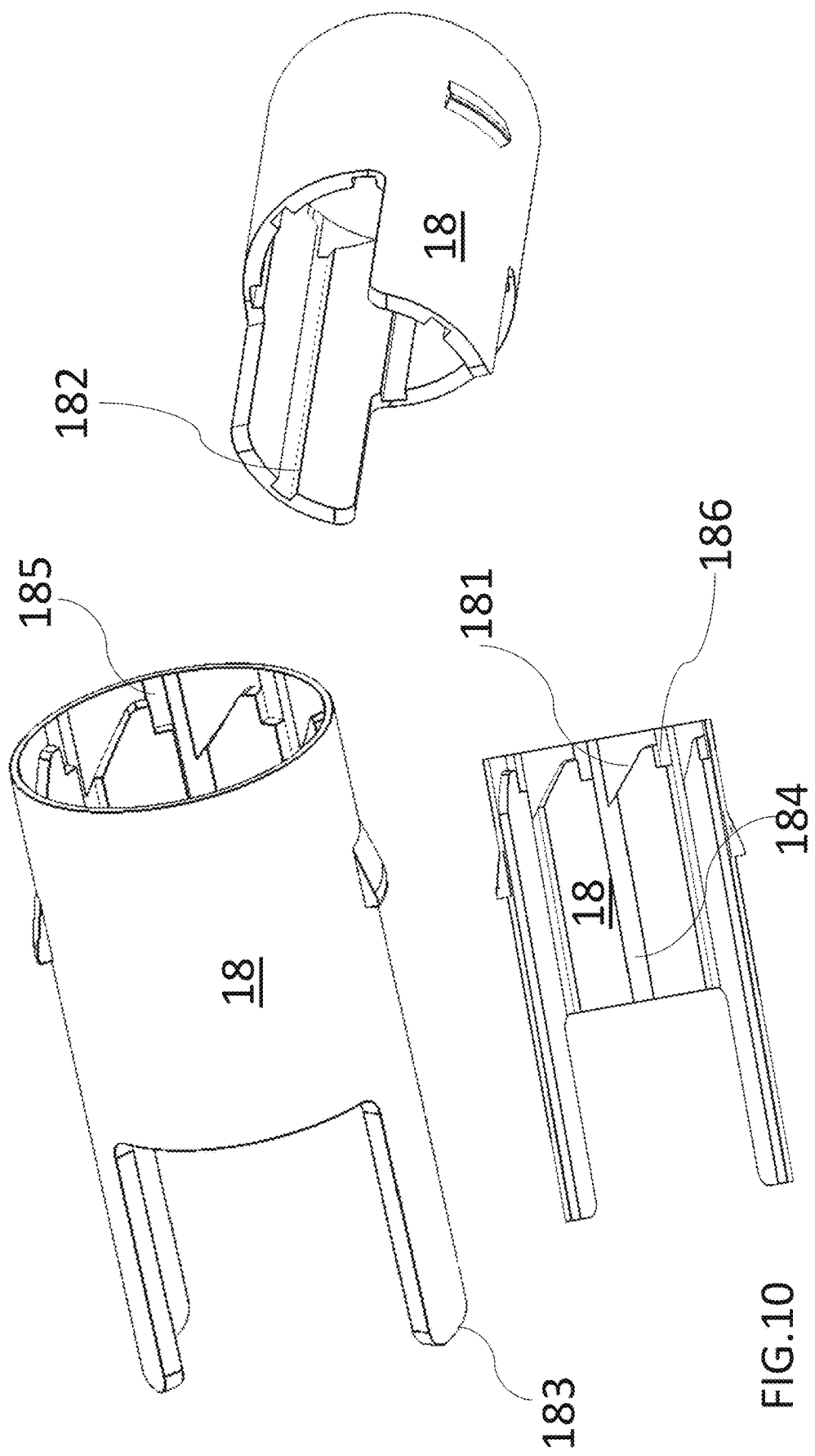
FIG. 10 shows two perspective views and one cross sectional view of the actuator base.

The actuator base 18 is illustrated in three different views in FIG. 10. The actuator base 18 can be a tubular component in the form of a shaped sleeve and comprises two distal cut outs forming two opposite distal tongues 183. On the inner circumferential surface of the actuator base 18 are arranged longitudinally extending grooves 182 configured to receive the longitudinal ribs 174 of the actuator sleeve 17. Since the actuator base 18 is fixedly connected to the housing 2, then the actuator sleeve 17 is prevented to rotate but may slide in relation to the actuator base 18. Also, at the proximal end on the inner circumferential surface of the actuator base 18 is arranged a guiding track forming a continuous sawtooth wave pattern track. The continuous sawtooth wave pattern track is formed by a slanted edge 181 where at its highest point passes to a longitudinally and proximally extending edge 184 and where at the lowest point of the longitudinally extending edge 184 passes to a minor slanted edge 185 and where at the highest point of the minor slanted edge 185 passes to a minor longitudinally and proximally extending edge 186. The function of the continuous sawtooth wave pattern track will be explained below.

Figure 11:
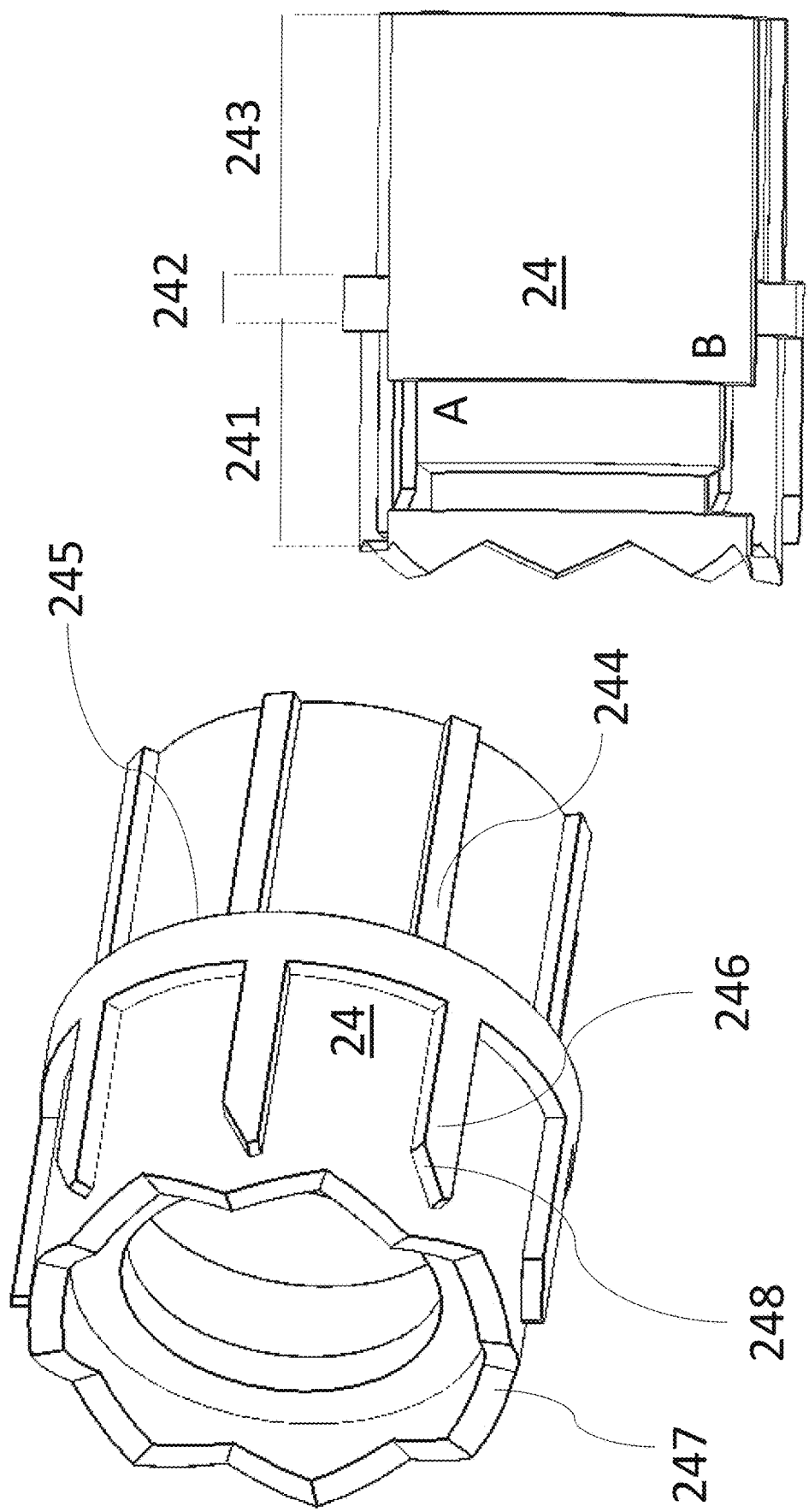
FIG. 11 illustrates a perspective and a cross-sectional view of the rotator sleeve.

The rotator sleeve 24, FIG. 11, comprises a distal part 241, a central part 242 and a proximal part 243 on its outer circumferential surface. The rotator sleeve 24 further comprises a first circumferential chamber A and a second circumferential chamber B on its inner circumferential surface. The distal part 241 is adapted to receive the proximal section of the actuator sleeve 17 such that the corresponding distal facing circumferential crown gear surface 247 matches with the proximal facing circumferential crown gear surface 171 of the actuator sleeve 17 i.e. the peaks are facing the troughs. The distal part 241 of the rotator sleeve 24 also comprises longitudinally and equidistant extending ribs 246 wherein each extending rib has a bevelled end surface 248 configured to interact with the slanted edges 181 on the inner circumferential surface of the actuator base 18. Thus, the distal part 241 is rotatably and slidably connected to both the actuator base 18 and to the actuator member 16. The first and the second circumferential chambers (A, B) on the inner circumferential surface of the rotator sleeve 24 are configured to interact with the second segment 169 of the actuator member 16 as will be explained below. The proximal part 243 of the rotator sleeve 24 comprises longitudinally and equidistant extending ribs 244 configured to interact with the locking protrusion 63 of the needle cover member 6, and the central part 242 of the rotator sleeve comprises a circumferential ledge 245 configured to interact with the distal edge 64 of the needle cover member 6.

Figure 12:
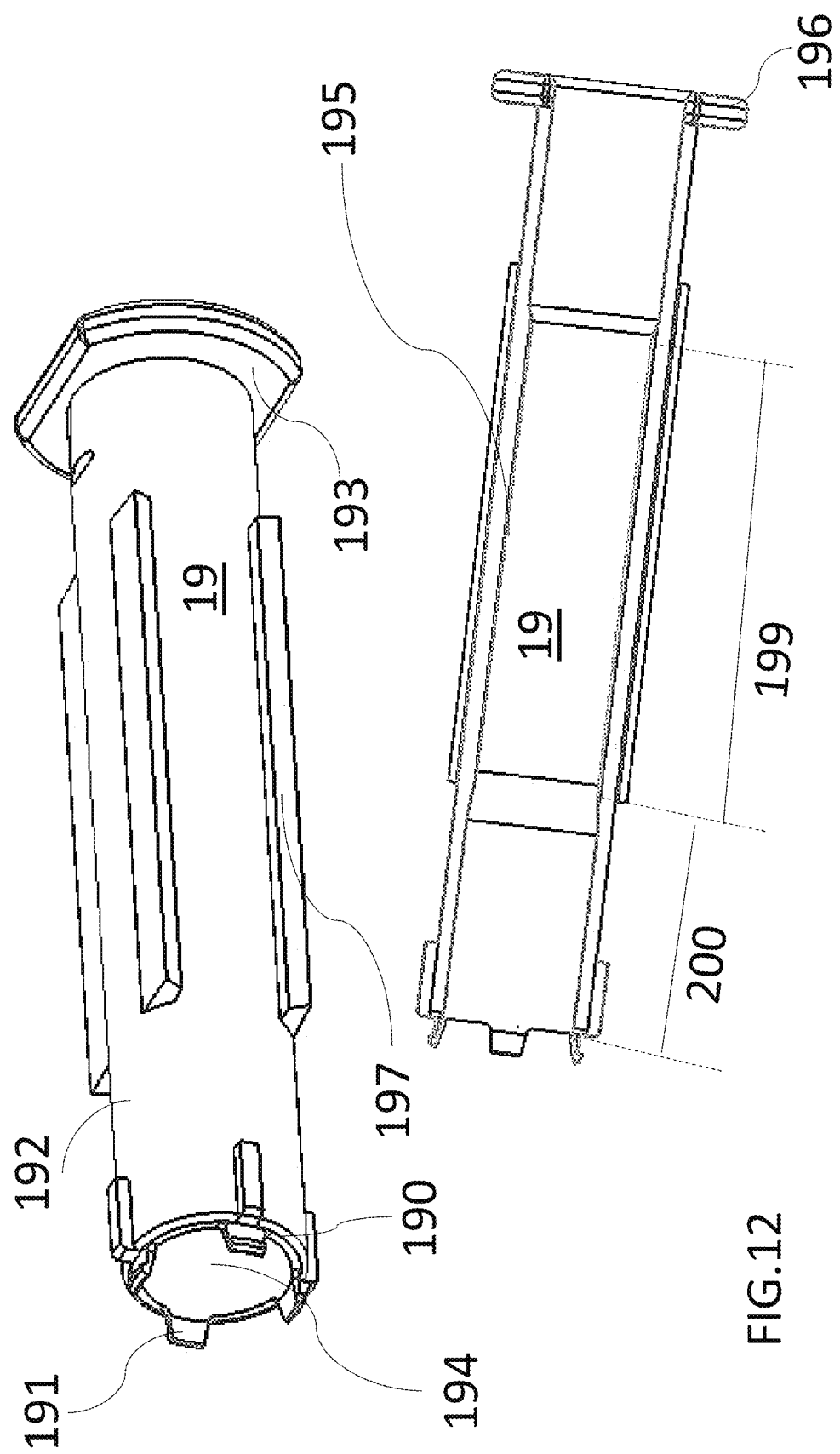
FIG. 12 illustrates a perspective and a cross-sectional view of the tubular demo container.

The tubular demo container 19 as shown in FIG. 12 simulates a medicament container in a real medicament delivery device. The demo container 19 may comprise a tubular body 192 having a proximal and transversal circumferential surface 190, which is washer-shaped, and a distal annular flange 193 having a distal end surface 196. The proximal and transversal circumferential surface 190 has a central opening 194 and equidistant proximally protruding engagement protrusions 191 configured to fixedly connect the demo container 19 to the inner surface of the elongated housing 2. Longitudinally extending ribs 197 are arranged on the tubular body 192 for guiding the container into the housing during assembly and for preventing rotation of the container in relation to the housing. The demo container 19 further comprises a tubular wall 195. In the present embodiment the tubular wall 195 is an inner tubular wall. The tubular wall 195 extends along the longitudinal axis L and is divided in two predetermined length portions. A distal portion 199 having a predetermined distal length and a predetermined distal diameter, and a second length 200 having a predetermined proximal length and a predetermined proximal diameter. The predetermined distal length 199 is larger than the predetermined proximal length 200 and the predetermined proximal diameter 200 is larger than the predetermined distal diameter 199.

The friction element 13 is configured to interact with the tubular wall 195 of the demo container 19 such that when the plunger 10 is released from the first position, a frictional resistive force between the friction element 13 and the tubular wall 195 of the demo container 19 causes the plunger 10 to be moved with a uniform speed and resistance simulating an injection phase of a medicament delivery. The first position is defined by a predetermined distance D (FIG. 14) between the proximal end 80 of the signal generating member 103 and the proximal surface 190 of the demo container 19 or the proximal surface of the elongated housing 2; and the second position is defined by the abutment between the proximal end 80 of the signal generating member 8 and the proximal surface 190 of the demo container 19 or the proximal surface of the elongated housing 2.

Figure 13:
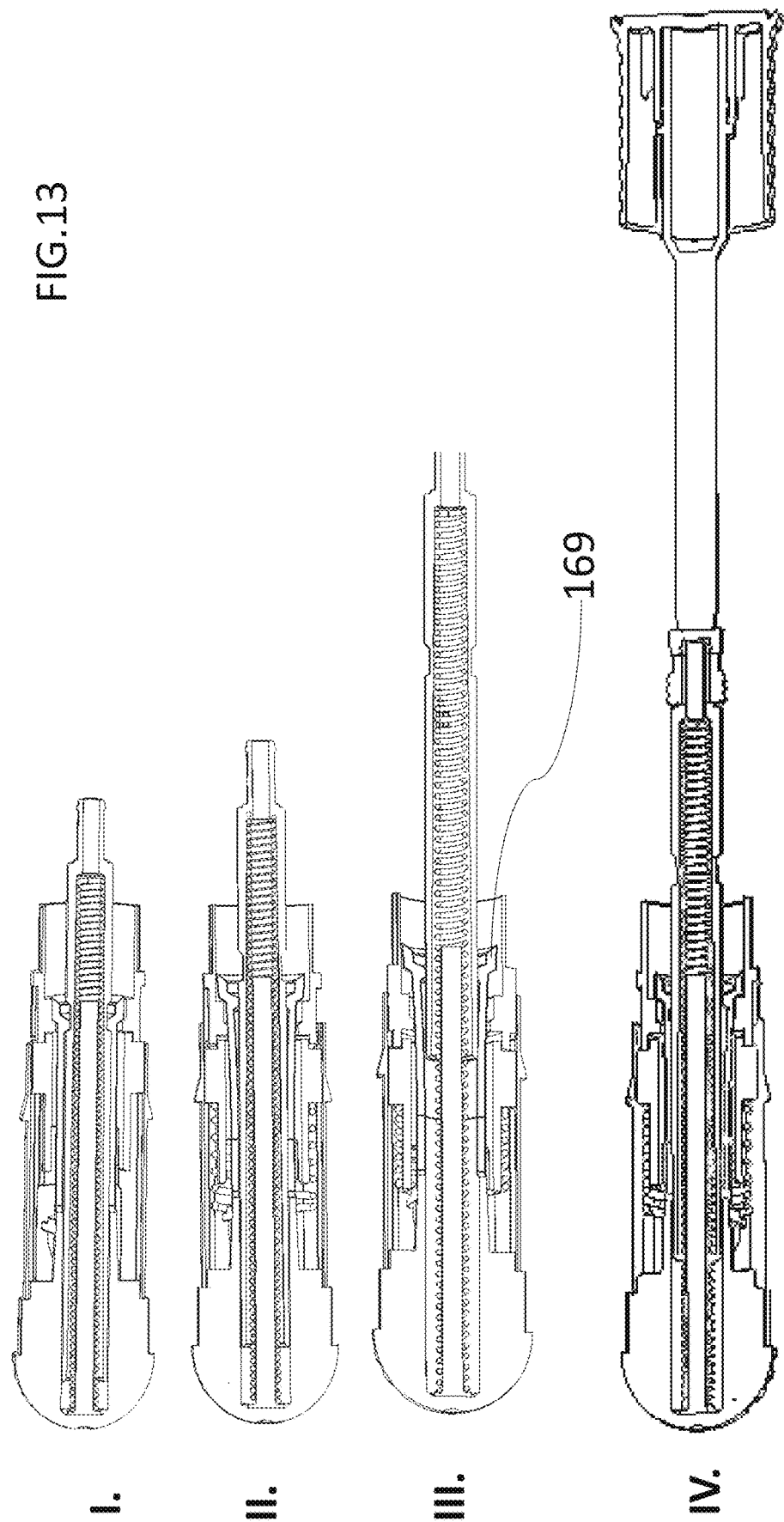
FIG. 13 depicts cross sectional views of selected parts of the embodiment in order to understand the mechanism behind the first audible signal.

FIG. 13 discloses sequentially the movement of the plunger 10 towards the proximal end 4 of the device and which is biased by the compressed first energy accumulating member is substantially inhibited by the inwardly directed ledge 164 of the actuator member 16 situated in the annular groove 104 of the plunger 10, and by the first circumferential chamber of the actuator sleeve 17 which overlaps at least part of the second segment 169 and inhibits the resilient portion 162 from moving in a radial outward direction when the actuator sleeve 17 is in the initial position. In other embodiments, the actuator 16 may be provided with an annular opening or recess instead of the inner protrusion 164 and the plunger 10 may be provided with an annular ledge instead of the annular groove 104. When the rotator sleeve 24 is moved towards the distal end by pressing the needle cover member against an intended injection site, the second segment 169 is released from the first circumferential chamber into the second circumferential chamber such that the second segment 169 is flexed radially outwards impacting the second circumferential chamber and causing a first audible feedback signal which simulates the start of an injection phase.

Figure 14:
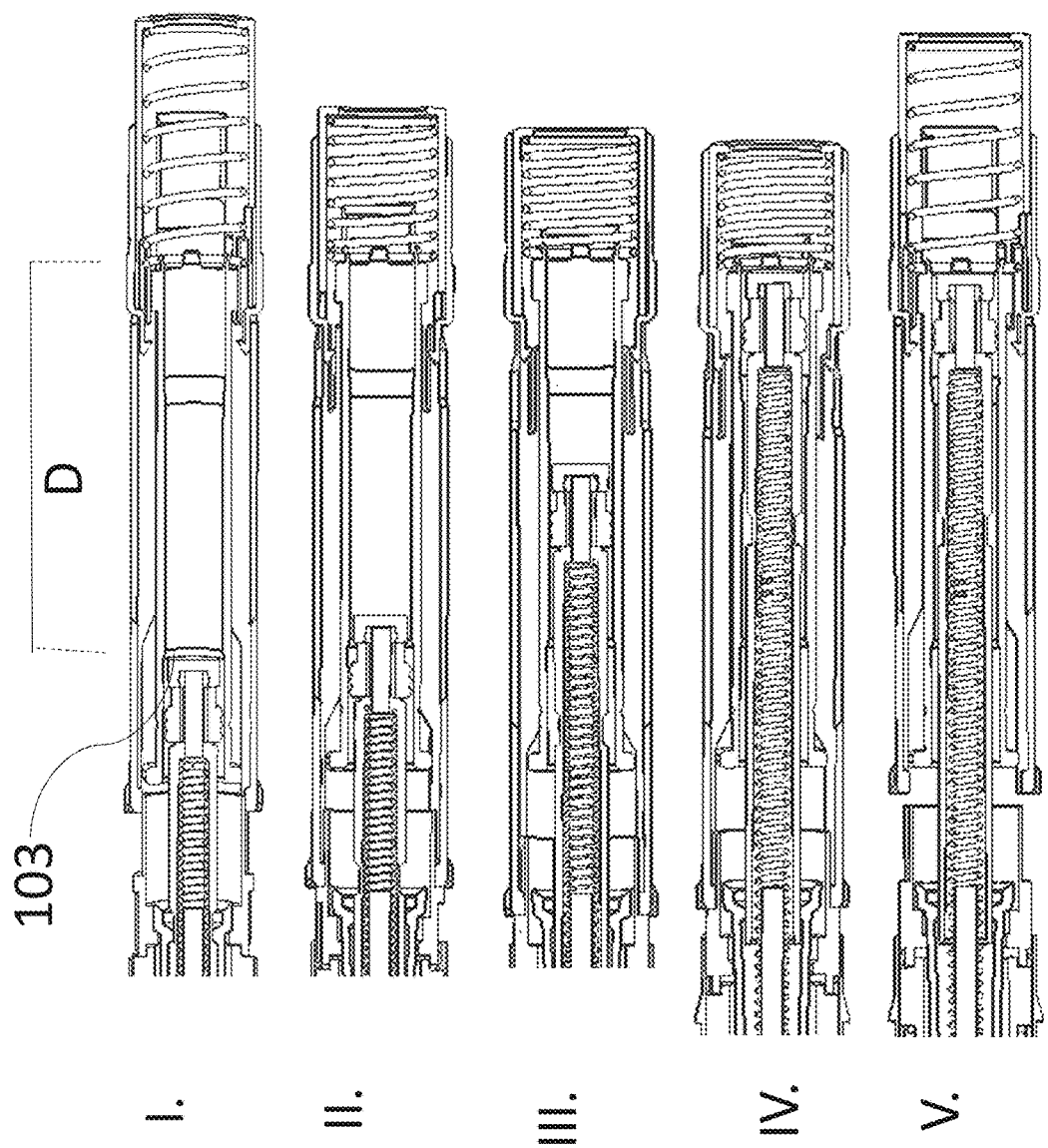
FIG. 14 illustrates cross sectional views of selected parts of the embodiment in order to understand the mechanism behind the second audible signal.

FIG. 14 discloses sequentially how the signal generating member 103 is configured to impact the proximal surface 190 of the demo container 19 or a proximal surface of the elongated housing 2 when the plunger 10 reaches the second position causing a second audible feedback signal which simulates the end of an injection phase. The tubular wall 195 and the friction element 13 are configured to be released from each other a predetermined distance before the plunger 10 reaches the second position causing the movement of the plunger 10 to be accelerated. This is achieved when the friction element 13 passes over from the distal portion 199 to the proximal portion 200 of the tubular wall 195 of the demo container 19. The friction element 13 is released from the distal portion 199 of the tubular wall and thus the plunger is accelerated.

As seen in FIGS. 15-18, the automatic injection training device 1 according to the embodiment of FIG. 1, is illustrated sequentially from the moment it is received by the end user (I) until the training device is completely reloaded (XII). Enlarged views of the engagement of the section around the crown gears (171, 247) are also provided. The actuator base 18 is transparent for the sake of clarity and in order to facilitate understanding over the rotatable mechanism of the automatic injection training device of the disclosure works during the training period.

Figure 15:
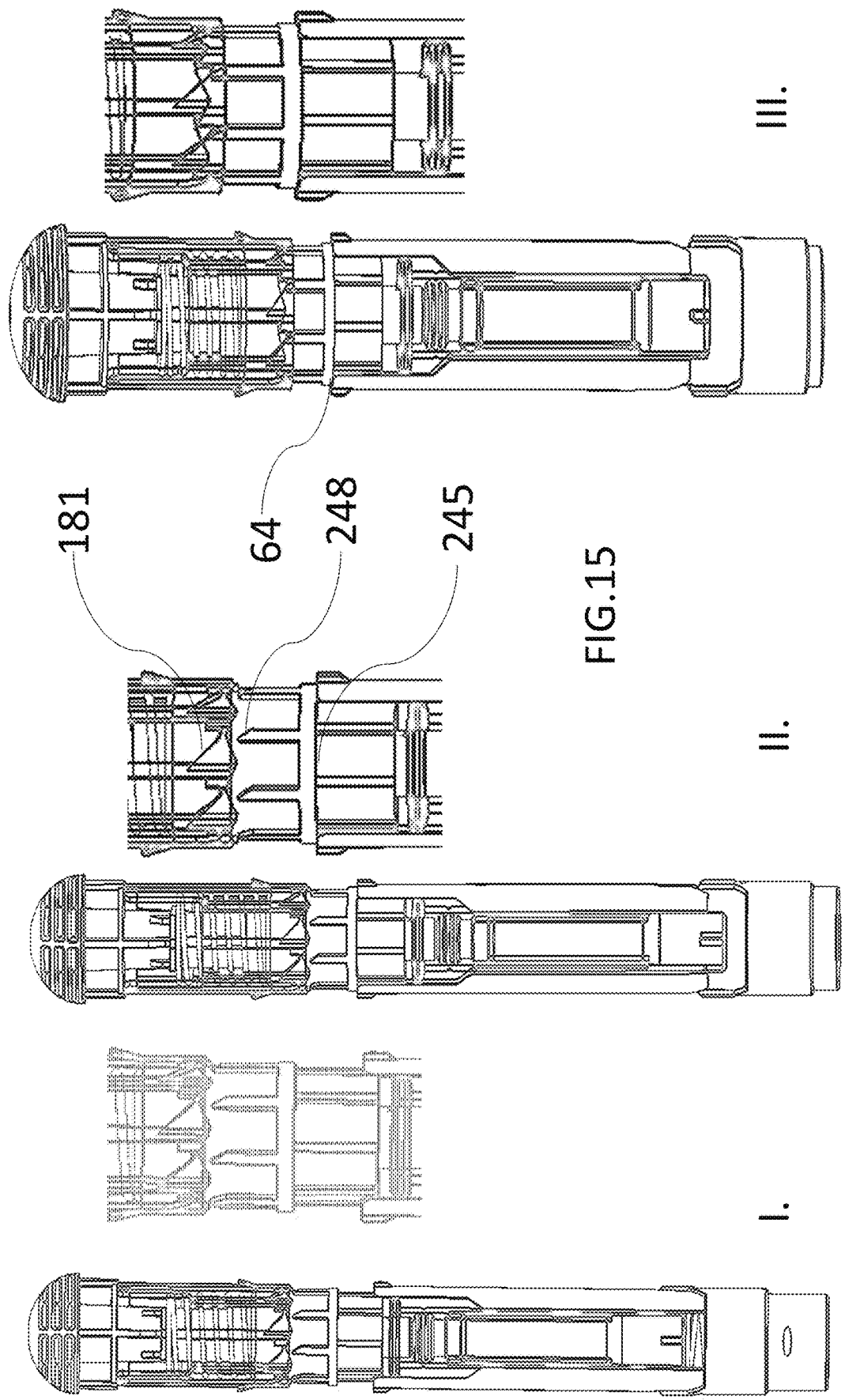
FIG. 15 (I, II, III), FIG. 16 (IV, V, VI), FIG. 17 (VII, VIII, IX) and FIG. 18 (X) are side views of the embodiment of the disclosure according to FIG. 1 without the elongated housing. The additional figures on the side are enlarged views of the crown gear zone, which depicts in more detail the mechanical sequence of the embodiment during use.

FIG. 15 (I, II, III); the reload cap unit 5 is removed such that the training device is ready for start the injection training. Subsequently, the user starts to push the proximal end of the needle cover 6 against an intended injection site whereby the needle cover 6 starts to be moved from the extended position wherein the distal edge 64 of the needle cover member 6 is positioned at predetermined distance from the circumferential ledge 245 of the rotator sleeve 24 (Sequence I), to a position wherein the distal edge 64 of the needle cover 6 is abutting the circumferential ledge 245 of the rotator sleeve 24 (sequence II). At this stage the longitudinally and equidistant extending ribs 244 of the rotator sleeve 24 are positioned besides the locking protrusions 63 of the needle cover member 6. A continuous pushing movement forces primarily the rotator sleeve 24 and the actuator sleeve 17 to move towards the distal end compressing the second energy accumulating member 25 and wherein the longitudinal ribs 174 of the actuator sleeve 17 slides into the longitudinally extending grooves 182 of the actuator base 18. Since the actuator base 18 is fixedly connected to the housing, then the actuator sleeve 17 is prevented to rotate and slides in relation to the actuator base 18. Also, the bevelled end surfaces 248 of the longitudinally and equidistant extending ribs 246 on the outer surface of the rotator sleeve 24 comes into contact with the slanted edges 181 on the inner circumferential surface of the actuator base 18, (Sequence III).

FIG. 16 (IV, V, VI), further pushing of the needle cover member 6 forces the bevelled end surfaces 248 of the longitudinally and equidistant extending ribs 246 on the outer surface of the rotator sleeve 24 to slide over the slanted edges 181 on the inner circumferential surface of the actuator base 18 such that the rotator sleeve 24 is forced to rotate in relation to the actuator sleeve 17 and the actuator base 18, whereby the peaks of the distal facing circumferential crown gear surface 247 of the rotator sleeve 24 slide over the slanted edges of the proximal facing circumferential crown gear surface 171 of the actuator sleeve 17 forcing the actuator sleeve to further slide towards the distal end in relation to the actuator base 18 until the peaks of the crown gear surfaces 171, 247 meets and passes over each other. At this stage, the inwardly directed ledge 164 of the actuator member 16 situated in the annular groove 104 of the plunger 10 is released since the actuator sleeve 17 is longitudinally moved towards the distal end and the first circumferential chamber of the actuator sleeve 17 is no longer overlapping at least part of the second segment 169 and inhibiting the resilient portion 162 from moving in a radial outward direction. The plunger 10 is forced by the compressed first energy accumulating member towards the proximal end of the device forcing the second segment 169 to be flexed radially outwards such that said second segment 169 impacts the second circumferential chamber causing the first audible feedback signal which simulates the start of an injection phase. The plunger 10 travels with a velocity along the L-axis through the tubular demo container 19. The friction element 13 of the plunger 10 keeps the velocity over the distal portion 199 and owing to the differences of diameters with the proximal portion 200 of the tubular wall 195 of the demo container 19 the plunger is accelerated when it passes from the distal portion 199 to the proximal portion 200. The plunger is stopped when the signal generating member impacts the proximal surface 190 of the demo container 19 or a proximal surface of the elongated housing 2 causing a second audible feedback signal which simulates the end of an injection phase.

FIG. 17 (VII, VIII, IX), the training device 1 is removed from the intended injection site and the needle cover member 6 is forced to slide back to the extended position by the third energy accumulation member 23 whereby distal part of the needle cover member 6 is separated from the proximal part 243 of the rotator sleeve 24 such that the locking protrusions 63 of the needle cover member 6 is separated from the longitudinally and equidistant extending ribs 244 and the distal edge 64 of the needle cover member 6 is separated from the circumferential ledge 245. At the same moment, the actuator sleeve 17 is forced by the second energy accumulating member 25 to slide towards the proximal end whereby the peaks of the proximal facing circumferential crown gear surface 171 slides over the slanted edges of the distal facing circumferential crown gear surface 247 forcing the rotator sleeve to rotate until the sides of longitudinally and equidistant extending ribs 246 on the outer surface of the rotator sleeve 24 meets the longitudinally and proximally extending edges 184 on the inner circumferential surface of the actuator base 18. The second energy accumulating member 25 continues to force the actuator sleeve 17 to slide towards the proximal end until the peaks of longitudinally and equidistant extending ribs 246 reach the minor slanted edges 185 on the inner circumferential surface of the actuator base 18 such that the peaks of the proximal facing circumferential crown gear surface 171 further slide over the slanted edges of the distal facing circumferential crown gear surface 247 for further forcing the rotator sleeve 24 to rotate until the upper sides of longitudinally and equidistant extending ribs 246 meets the minor longitudinally and proximally extending edges 186 on the inner circumferential surface of the actuator base 18. Also at this stage, the locking protrusions 63 of the needle cover member 6 are besides the next longitudinally and equidistant extending ribs 244 of the rotator sleeve 24 since the rotator sleeve 24 has been rotated. These abutments prevent the rotator sleeve to continue to rotate. Then the rotator sleeve is locked. If further attempts to push the needle cover member 6 against an intended injection site are made, the locking protrusions 63 of the needle cover member 6 will abut the longitudinally and equidistant extending ribs 244. Thus the needle cover member 6 will be maintained in a locked state.

FIG. 18 (X, XI, XII) the injection training performance is ended in sequence X accordingly. The needle cover 6 distal edge 64 is detached of the rotator sleeve 24, which in turn is locked by the abutment compression between the actuator base 18 and the actuator sleeve 17. Furthermore, the training device 1 is connected to the reload cap unit 5 (Sequence XI). The shaft 71 is connected to the plunger 10 via the signal generating member 103 proximal part 80 through the demo container 19 creating a third audible feedback signal. The hollow plunger 10 and the shaft member 71 will be moved in the distal direction against the axial force of the first energy accumulating member 11 until the annular groove 104 of the hollow plunger 10 engages with the annular inwardly directed ledge 164 of the actuator member 16 whereby the second energy accumulating member 25 will force the actuator sleeve 17 back into its initial position since the peaks of the proximal facing circumferential crown gear surface 171 continue to slide over the slanted edges of the distal facing circumferential crown gear surface 247 for further forcing the rotator sleeve 24 to slide towards the proximal end and to rotate until the peaks of longitudinally and equidistant extending ribs 246 passes the lowest part of the minor longitudinally and proximally extending edges 186 on the inner circumferential surface of the actuator base 18 and the peaks of the proximal facing circumferential crown gear surface 171 faces the troughs of the distal facing circumferential crown gear surface 247. The training device 1 reload process is finished and the device 1 is ready for training injection again returning to the initial sequence 1 (Sequence XII), ready for the user next training session.

Furthermore, in the claims, the word "comprising" does not exclude other elements or steps, and the indefinite article "a" or "an" does not exclude a plurality. A single unit may fulfil the functions of several features recited in the claims. The terms "essentially", "about", "approximately" and the like in connection with an attribute or a value particularly also define exactly the attribute or exactly the value, respectively. Any reference signs in the claims should not be considered as limiting the scope.

It is however to be understood that embodiments described above and shown in the drawings are to be regarded only as non-limiting examples of the present disclosure and that may be modified within the scope of the appended patent claims.

The invention claimed is:

1. An automatic injection training device comprising:
an elongated housing having a distal and an opposite proximal end and extending along a longitudinally axis;
a tubular demo container axially and rotationally fixed relative to the elongated housing and having a tubular wall extending along the longitudinally axis;
a reloadable plunger assembly comprising a plunger that has an annular groove, is hollow and has an annular heel located on an inner surface of the plunger, where the plunger is movable in the demo container between a first and a second position and a first spring positioned inside the plunger and biased against the annular heel to move the plunger from the first to the second position;
an actuation assembly comprising a resilient portion having a central opening configured to receive the plunger, where the resilient portion is releasably engaged with the annular groove to hold the plunger in the first position;

a rotator sleeve operatively engaged with a rotationally locked actuation sleeve in the actuation assembly to provide controlled rotation of the rotator sleeve relative to the actuation sleeve and the housing;

a needle cover assembly comprising a needle cover that is biased in a proximal direction and which is movable in relation to the rotator sleeve and the housing from an extended position to a retracted position and from the retracted position to the extended position, wherein the needle cover is configured to interact with the actuation assembly to release the plunger when the needle cover is moved from the extended position to the retracted position and wherein the needle cover engages the rotator sleeve such that the needle cover is prevented from retracting after the needle cover is moved from the retracted position to the extended position.

2. The automatic injection training device according to claim 1, wherein the actuation assembly comprises an actuator and an actuator base which are fixedly connected to the elongated housing, where the actuator sleeve is configured to interact with the actuator base, a second spring arranged between the actuator sleeve and the actuator, and the rotator sleeve configured to interact with both the actuator and the actuator base, and with the actuator sleeve.

3. The automatic injection training device according to claim 2, wherein the biased needle cover assembly further comprises a third spring for urging the needle cover towards the proximal end of the elongated housing such that a proximal portion end of the needle cover protrudes from the proximal end of the elongated housing, and wherein the needle cover has a distal edge and a locking protrusion that is operationally associated with the rotator sleeve to prevent the retraction of the needle cover when moved from the retracted position to the extended position.

4. The automatic injection training device according to claim 2, wherein the actuator sleeve is rotationally locked but axially movable in relation to the actuator base and operationally associated with the second spring such that, the actuator sleeve is axially moveable in relation to the actuator base against an axial force from said second spring.

5. The automatic injection training device according to claim 2, wherein the resilient portion comprises a first segment, a second segment, and a tapering segment between the first segment and the second segment, and an annular inwardly directed ledge.

6. The automatic injection training device according to claim 5, wherein the rotator sleeve comprises an outer surface having a distal part, a central part and a proximal part, where the rotator sleeve has a first circumferential chamber and a second circumferential chamber located on an inner surface of the rotator sleeve, wherein the distal part is rotatable and slidably connected to both the actuator base and to the actuator and wherein the first and the second circumferential chambers are configured to interact with the second segment of the actuator.

7. The automatic injection training device according to claim 6, wherein the proximal part of the rotator sleeve comprises longitudinally and equidistant extending ribs configured to interact with the locking protrusion of the needle cover, wherein the central part of the rotator sleeve comprises a circumferential ledge configured to interact with the distal edge of the needle cover, and wherein the distal part of the rotator sleeve comprises a distal facing circumferential crown gear surface configured to interact with a corresponding proximal facing circumferential crown gear surface of the actuator sleeve, and longitudinally and equidistant extending ribs configured to interact with a guiding track on the inner surface of the actuator base.

8. The automatic injection training device according to claim 6, wherein the guiding track of the actuator base is a continuous sawtooth wave pattern track formed by a slanted edge where at its highest point passes to a longitudinally and proximally extending edge and where at the lowest point of the longitudinally extending edge passes to a minor slanted edge and where at the highest point of the minor slanted edge passes to a minor longitudinally and proximally extending edge.

9. The automatic injection training device according to claim 6, wherein the second segment of the actuator is configured to interact with the first circumferential chamber of the rotator sleeve such that the annular inwardly directed ledge is engaged with the annular slot of the plunger for holding the plunger in the first position and wherein the second segment of the actuator is configured to interact with the second circumferential chamber when the rotator sleeve is moved towards the distal end by pressing the needle cover against an intended injection site, such that the second segment is flexed radially outwards impacting the second circumferential chamber for causing a first audible feedback signal which simulates the start of an injection phase.

10. The automatic injection training device according to claim 1, wherein the device further comprises a signal generator which is fixedly connected to the proximal end of the plunger and configured to impact a proximal surface of the demo container or a proximal surface of the elongated housing when the proximal end of the plunger reaches the second position causing a second audible feedback signal which simulates the end of an injection phase.

11. The automatic injection training device according to claim 1, wherein the plunger comprises a sliding stopper configured to interact with the tubular wall of the demo container such that when the plunger is released from the first position, a frictional resistive force between the sliding stopper and the tubular wall of the demo container causes the plunger to be moved with a uniform speed and resistance simulating an injection phase of a medicament delivery.

12. The automatic injection training device according to claim 11, wherein the tubular wall of the demo container and the sliding stopper are configured to be released from each other a predetermined distance before the plunger reaches the second position causing the movement of the plunger to be accelerated.

13. The automatic injection training device according to claim 1, wherein the plunger is axially moveable in relation to the elongated housing towards the distal end of the elongation housing from the second position to the first position against the axial force from the first spring.

14. An assembly comprising an automatic injection training device according to claim 1 having a reload cap unit wherein the reload cap unit comprises a removable proximal cap having a shaft member that is configured for being introduced into the elongated housing assembly through a proximal opening of the needle cover.

15. The assembly according to claim 14, wherein the removable proximal cap comprises a first portion with a cup-shaped structure that is configured to accommodate and/or guide the proximal portion end of the needle cover that extends from the proximal end of the elongated housing and that is configured to bear against an abutment surface of the elongated housing assembly when the device is reloaded.

16. An automatic injection training device comprising:
- an elongated housing having a distal and an opposite proximal end and extending along a longitudinally axis;
- a tubular demo container axially and rotationally fixed relative to the elongated housing, where the demo container does not contain a medicament and has a tubular wall open at both a distal end and a proximal end that extends along the longitudinally axis;
- a reloadable plunger assembly comprising a plunger that has an annular slot, is hollow and has an annular heel located on an inner surface of the plunger, where the plunger is movable in the demo container between a first and a second position; and
- a first spring positioned inside the plunger and biased against the annular heel to move the plunger from the first to the second position;
- an actuation assembly comprising an actuation sleeve and a resilient portion having a central opening configured to receive the plunger, where the resilient portion is releasably engaged with the annular groove to hold the plunger in the first position;
- a rotator sleeve operatively engaged with the actuation sleeve through a crown gear to provide controlled rotation of the rotator sleeve relative to the housing; and
- a needle cover movable in relation to the housing from an extended position to a retracted position, where movement of the needle cover relative to the housing causes the plunger to move proximally inside the demo container,
- wherein a distal end of the cover the needle cover interacts with the rotator sleeve to form a locking engagement to prevent the needle cover from retracting after the needle cover is moved from a retracted position to an extended position.

17. The automatic injection training device according to claim 16, wherein the plunger further comprises a sliding stopper that engages the tubular wall when the plunger moves proximally to create a frictional resistive force between the sliding stopper and the tubular wall that causes the plunger to be moved with a uniform speed and resistance simulating an injection phase of a medicament delivery.

18. The automatic injection training device according to claim 16, further comprising a reload cap unit having a removable proximal cap and a shaft member that fits into the elongated housing assembly through a proximal opening of the needle cover and through the open proximal end of the demo container.

19. The automatic injection training device according to claim 18, further comprising a signal generator positioned on the proximal end of the plunger that impact a proximal surface of the demo container or a proximal surface of the elongated housing causing an audible or tactile feedback signal that simulates the end of an injection phase.

20. The automatic injection training device according to claim 16 further comprising a signal generator that generates an audible or tactile feedback signal simulating the start of an injection phase when the needle cover is pressed against an intended injection site.

* * * * *